（12） United States Patent
Eisenberg et al.

(10) Patent No.: US 10,934,332 B2
(45) Date of Patent: Mar. 2, 2021

(54) STRUCTURE-BASED PEPTIDE INHIBITORS THAT TARGET THE TAU VQIINK FIBRILLIZATION SEGMENT

(71) Applicant: THE REGENTS OF THE UNIVERSITY OF CALIFORNIA, Oakland, CA (US)

(72) Inventors: David S. Eisenberg, Los Angeles, CA (US); Paul M. Seidler, Los Angeles, CA (US); David R. Boyer, Santa Monica, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 16/489,294

(22) PCT Filed: Mar. 15, 2018

(86) PCT No.: PCT/US2018/022742
§ 371 (c)(1),
(2) Date: Aug. 27, 2019

(87) PCT Pub. No.: WO2018/170324
PCT Pub. Date: Sep. 20, 2018

(65) Prior Publication Data
US 2020/0017563 A1 Jan. 16, 2020

Related U.S. Application Data

(60) Provisional application No. 62/471,831, filed on Mar. 15, 2017.

(51) Int. Cl.
C07K 7/00 (2006.01)
C07K 14/00 (2006.01)
C07K 5/00 (2006.01)
C07K 4/00 (2006.01)
A61K 38/00 (2006.01)
A61K 49/00 (2006.01)
C07K 14/475 (2006.01)
C07K 14/48 (2006.01)
C07K 14/47 (2006.01)
A61K 38/17 (2006.01)
A61K 38/18 (2006.01)
A61K 38/19 (2006.01)
A61K 38/20 (2006.01)
(Continued)

(52) U.S. Cl.
CPC .......... C07K 14/4711 (2013.01); A61K 38/08 (2013.01); A61K 38/10 (2013.01); A61K 38/1709 (2013.01); A61K 38/1716 (2013.01); A61P 25/28 (2018.01); C07K 14/47 (2013.01); A61K 38/00 (2013.01); A61K 38/16 (2013.01); A61K 39/0007 (2013.01); A61K 47/64 (2017.08); A61K 47/645 (2017.08); A61K 49/0056 (2013.01); A61K 51/08 (2013.01); A61P 25/00 (2018.01); A61P 25/02 (2018.01); C07K 7/06 (2013.01); C07K 7/08 (2013.01); C07K 14/435 (2013.01); C07K 2317/24 (2013.01); C07K 2317/34 (2013.01); C07K 2319/00 (2013.01); C07K 2319/10 (2013.01); C12N 9/6421 (2013.01); G01N 33/6896 (2013.01); G01N 2333/4709 (2013.01); G01N 2800/28 (2013.01); G01N 2800/2814 (2013.01); G01N 2800/2821 (2013.01); G01N 2800/2835 (2013.01)

(58) Field of Classification Search
CPC ....... G01N 33/6896; G01N 2800/2821; G01N 2800/50; G01N 2800/7047; C07K 2317/24; C07K 2317/34; C07K 14/4711; C07K 2317/70; C07K 2317/76; C07K 2317/92; C07K 2317/94; C07K 7/06; C07K 7/08; C07K 14/47; C07K 2319/00; A61K 38/1709; A61K 39/3955; A61K 38/08; A61K 38/1716; A61K 51/08
See application file for complete search history.

(56) References Cited

U.S. PATENT DOCUMENTS 7,964,556 B1 * 6/2011 Kobayashi ............. A61K 38/08
424/1.69
2006/0122122 A1 * 6/2006 Kobayashi ............. A61K 38/08
514/2.4
2011/0144029 A1 6/2011 D'Mello et al.

FOREIGN PATENT DOCUMENTS

WO 2001018546 3/2001

OTHER PUBLICATIONS

Burgess et al. J of Cell Bio. 1990, 111:2129-2138.*
Bowie et al. Science, 1990, 247:1306-1310.*
Pawson et al. 2003, Science 300:445-452.*
Alaoui-Ismaili et al., Cytokine Growth Factor Rev. 2009; 20:501-507.*

(Continued)

Primary Examiner — Chang-Yu Wang
(74) Attorney, Agent, or Firm — Gates & Cooper LLP

(57) ABSTRACT

Aggregated Tau protein is associated with over 20 neurological disorders including Alzheimer's disease. Previous work has shown that Tau's sequence segments VQIINK (SEQ ID NO: 11) and VQIVYK (SEQ ID NO: 9) drive its aggregation, and that inhibitors based on the structure of the VQIVYK (SEQ ID NO: 9) segment partially inhibit Tau aggregation. Here we show that the VQIINK (SEQ ID NO: 11) segment is the more powerful driver of Tau aggregation. Two structures of this segment determined by the cryo EM method MicroED explain its more powerful seeding. Of practical significance, the understanding of the structures has led to the design of structure based peptide inhibitors that effectively inhibit Tau aggregation as well as the ability of exogenous Tau fibrils to seed intracellular Tau in mammalian cells into amyloid.

10 Claims, 12 Drawing Sheets
Specification includes a Sequence Listing.

(51) Int. Cl.

| | | |
|---|---|---|
| A61K 38/21 | (2006.01) | |
| A61P 25/28 | (2006.01) | |
| A61K 38/08 | (2019.01) | |
| A61K 38/10 | (2006.01) | |
| C07K 14/435 | (2006.01) | |
| C07K 7/06 | (2006.01) | |
| C12N 9/64 | (2006.01) | |
| C07K 7/08 | (2006.01) | |
| A61P 25/00 | (2006.01) | |
| A61P 25/02 | (2006.01) | |
| G01N 33/68 | (2006.01) | |
| A61K 51/08 | (2006.01) | |
| A61K 38/16 | (2006.01) | |
| A61K 47/64 | (2017.01) | |
| A61K 39/00 | (2006.01) | |

(56) References Cited

OTHER PUBLICATIONS

Guo et al., PNAS 2004; 101:9205-9210.*
Mori et al. Biochem. Biophys. Res. Commun. 1989; 159:1221-1226.*
Lee et al. Neuron. 1989; 2:1615-1624.*
PCT International Search Report & Written Opinion dated Aug. 9, 2018, International Application No. PCT/US18/22742.
Uniprot A0A1G4IZM5. LAME_0C01838g1_1. [online] Feb. 15, 2017 [retrieved Jun. 11, 2018]. Available on the Internet: < https://www.uniprot.org/uniprot/A0A1G4IZM5.txt?version=2>. Especially p. 1.
Sievers et al., "Structure-based design of non-natural amino-acid inhibitors of amyloid fibril formation".Nature, vol. 475, Jul. 7, 2011, pp. 96-100.

\* cited by examiner

SEQUENCE LISTING

```
<160> NUMBER OF SEQ ID NOS: 32

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Val Gln Ile Ile Asn Lys Lys Leu Asp
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Val Gln Met Ile Asn Lys Lys Arg Lys
1               5                   10
```

<210> SEQ ID NO 3
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Val Gln Trp Ile Asn Lys Lys Arg Lys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asp Val Gln Arg Ile Asn Lys Lys Arg Lys
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Asp Val Trp Met Ile Asn Lys Lys Arg Lys
1               5                   10

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asp Val Trp Trp Ile Asn Lys Lys Arg Lys
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Asp Val Trp Met Trp Asn Lys Lys Arg Lys
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Asp Val Trp Trp Trp Asn Lys Lys Arg Lys
1               5                   10

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Val Gln Ile Val Tyr Lys
1               5

<210> SEQ ID NO 10
<211> LENGTH: 440
<212> TYPE: PRT
<213> ORGANISM: Homo sapiens

<400> SEQUENCE: 10

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln

```
                275                 280                 285
Ser Lys Cys Gly Ser Lys Asp Asn Ile Lys His Val Pro Gly Gly Gly
    290                 295                 300
Ser Val Gln Ile Val Tyr Lys Pro Val Asp Leu Ser Lys Val Thr Ser
305                 310                 315                 320
Lys Cys Gly Ser Leu Gly Asn Ile His His Lys Pro Gly Gly Gly Gln
                325                 330                 335
Val Glu Val Lys Ser Glu Lys Leu Asp Phe Lys Asp Arg Val Gln Ser
            340                 345                 350
Lys Ile Gly Ser Leu Asp Asn Ile Thr His Val Pro Gly Gly Gly Asn
                355                 360                 365
Lys Lys Ile Glu Thr His Lys Leu Thr Phe Arg Glu Asn Ala Lys Ala
        370                 375                 380
Lys Thr Asp His Gly Ala Glu Ile Val Tyr Lys Ser Pro Val Val Ser
385                 390                 395                 400
Gly Asp Thr Ser Pro Arg His Leu Ser Asn Val Ser Ser Thr Gly Ser
                405                 410                 415
Ile Asp Met Val Asp Ser Pro Gln Leu Ala Thr Leu Ala Asp Glu Val
                420                 425                 430
Ser Ala Ser Leu Ala Lys Gln Gly
            435                 440

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Val Gln Ile Ile Asn Lys
1               5

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Val Gln Ile Val Ile Tyr Lys
1               5

<210> SEQ ID NO 13
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(16)
<223> OTHER INFORMATION: This sequence may encompass 5-16 residues
<220> FEATURE:
<223> OTHER INFORMATION: See specification as filed for detailed
      description of substitutions and preferred embodiments

<400> SEQUENCE: 13

Arg Arg Arg Arg Arg Arg Arg Arg Arg Arg Arg Arg Arg Arg Arg Arg
```

```
<210> SEQ ID NO 14
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Arg Gly Gly Arg Leu Ser Tyr Ser Arg Arg Phe Ser Thr Ser Thr
1               5                   10                  15

Gly Arg

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Arg Arg Leu Ser Tyr Ser Arg Arg Arg Phe
1               5                   10

<210> SEQ ID NO 16
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Arg Gln Ile Lys Ile Trp Phe Gln Asn Arg Arg Met Lys Trp Lys Lys
1               5                   10                  15

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Gln Ile Arg Ile Trp Phe Gln Asn Arg Arg Met Arg Trp Arg Arg
1               5                   10                  15

<210> SEQ ID NO 18
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Lys Gln Ile Lys Ile Trp Phe Gln Asn Lys Lys Met Lys Trp Lys Lys
1               5                   10                  15

<210> SEQ ID NO 19
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 19

Gly Arg Lys Lys Arg Arg Gln Arg Arg Pro Trp Gln
1               5                   10

<210> SEQ ID NO 20
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Gly Arg Lys Lys Arg Arg Gln Arg Arg Pro Pro Gln
1               5                   10

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Gly Arg Arg Arg Arg Arg Arg Arg Arg Pro Pro Gln
1               5                   10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Tyr Gly Arg Lys Lys Arg Arg Gln Arg Arg Arg
1               5                   10

<210> SEQ ID NO 23
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(13)
<223> OTHER INFORMATION: D-amino acid

<400> SEQUENCE: 23

Gly Arg Lys Lys Arg Arg Gln Arg Arg Pro Pro Gln
1               5                   10

<210> SEQ ID NO 24
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24
```

```
Lys Met Thr Arg Ala Gln Arg Arg Ala Ala Arg Arg Asn Arg Trp
1               5                   10                  15

Thr Ala Arg

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Lys Val Pro Asp
1

<210> SEQ ID NO 26
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Leu Asp Leu Ser Asn
1               5

<210> SEQ ID NO 27
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(16)
<223> OTHER INFORMATION: This sequence may encompass 5-16 residues
<220> FEATURE:
<223> OTHER INFORMATION: See specification as filed for detailed
      description of substitutions and preferred embodiments

<400> SEQUENCE: 27

Lys Lys Lys Lys Lys Lys Lys Lys Lys Lys Lys Lys Lys Lys Lys Lys
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(16)
<223> OTHER INFORMATION: This sequence may encompass 1-16 residues
<220> FEATURE:
<223> OTHER INFORMATION: See specification as filed for detailed
      description of substitutions and preferred embodiments

<400> SEQUENCE: 28

Arg Arg Arg Arg Arg Arg Arg Arg Arg Arg Arg Arg Arg Arg Arg Arg
1               5                   10                  15

<210> SEQ ID NO 29
<211> LENGTH: 31
```

```
<212> TYPE: PRT
<213> ORGANISM: Homo sapiens

<400> SEQUENCE: 29

Lys Val Gln Ile Ile Asn Lys Lys Leu Asp Leu Ser Asn Val Gln Ser
1               5                   10                  15

Lys Cys Gly Ser Lys Asp Asn Ile Lys His Val Pro Gly Gly Gly
                20                  25                  30

<210> SEQ ID NO 30
<211> LENGTH: 31
<212> TYPE: PRT
<213> ORGANISM: Homo sapiens

<400> SEQUENCE: 30

Ser Val Gln Ile Val Tyr Lys Pro Val Asp Leu Ser Lys Val Thr Ser
1               5                   10                  15

Lys Cys Gly Ser Leu Gly Asn Ile His His Lys Pro Gly Gly Gly
                20                  25                  30

<210> SEQ ID NO 31
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Lys Lys Leu Asp
1

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Val Gln Ile Tyr Val Lys
1               5
```

STRUCTURE-BASED PEPTIDE INHIBITORS THAT TARGET THE TAU VQIINK FIBRILLIZATION SEGMENT

CROSS-REFERENCE TO RELATED APPLICATIONS

This application is a national stage application, filed under 35 U.S.C. 371, of International Patent Application No. PCT/US18/22742, filed on Mar. 15, 2018, by David S. Eisenberg, et al., which claims priority under Section 119(e) from U.S. Provisional Application Ser. No. 62/471,831, filed Mar. 15, 2017, the contents of which are incorporated herein by reference.

STATEMENT AS TO RIGHTS TO INVENTIONS MADE UNDER FEDERALLY SPONSORED RESEARCH AND DEVELOPMENT

This invention was made with government support under Grant Numbers AG029430, AG061847 and NS095661, awarded by the National Institutes of Health. The government has certain rights in the invention.

TECHNICAL FIELD

The invention relates to compositions and methods useful in inhibiting aggregation of Tau protein.

BACKGROUND OF THE INVENTION

Tau protein assembles into oligomers and amyloid fibers that are hallmark to over twenty neurological disorders including Alzheimer's disease (AD). The 441-residue protein Tau is abundant in neurons where in its native state it is bound to microtubules. In solution Tau is largely unfolded[1,2], and in the numerous neuropathologies known as tauopathies, Tau is aggregated into amyloid fibrils.[3] The most prevalent tauopathy is Alzheimer's disease, where aggregated Tau is found as intracellular "tangles" first reported by Alzheimer. Until recently, tangles were observed only in stained brain sections upon autopsy. The development of PET probes is helping to illuminate the course of AD progression, and it is becoming evident that cognitive decline in AD is tightly coupled to the appearance of Tau aggregates in the brain.[4] Furthermore evidence suggests that amyloid β plaques can form early on and may set the stage for Tau aggregation and disease progression.[5-7]

In normal neurons, Tau promotes microtubule stability by binding tubulin through its microtubule binding domain (K18) comprised of four imperfect repeats. Six Tau isoforms encode variable architectures, the longest of which contains all four repeats (4R) whereas a shorter isoform with 3 repeats (3R) lacks repeat 2. Driving the formation of amyloid aggregates of Tau are two six-residue segments, VQI-INK (SEQ ID NO: 11) at the start of Repeat 2 and VQIVYK (SEQ ID NO: 9) at the start of Repeat 3 (FIG. 1A).[2,8]

Highly specific inhibitors of Tau aggregation are needed to definitively determine if, and how Tau aggregates lead to cognitive decline in AD and other tauopathies. The atomic structure of an amyloid fibril formed by the VQIVYK (SEQ ID NO: 9) segment of Repeat 3 was determined in 2007[9] and the structure was used to design inhibitors of aggregation of VQIVYK (SEQ ID NO: 9) and a construct containing 3 repeats (with VQIVYK (SEQ ID NO: 9) but not VQIINK (SEQ ID NO: 11)).[10,11] These studies demonstrated that VQIVYK (SEQ ID NO: 9) inhibitors can block aggregation of 3R Tau isoforms in vitro but are less effective at inhibiting 4R isoforms including full-length Tau40, which additionally contains the VQIINK (SEQ ID NO: 11) segment of Repeat 2. Efforts over a decade to grow crystals of amyloid fibrils of VQIINK (SEQ ID NO: 11) produced only nano-crystals, far too small for single crystal X-ray diffraction. Consequently, there is a need for an understanding of the structure of these molecules, particularly information which allows the design of functional inhibitors.

SUMMARY OF THE INVENTION

Two hexapeptides, VQIINK (SEQ ID NO: 11) and VQIVYK (SEQ ID NO: 9) are critical for the formation of Tau aggregates, aggregates which are associated with a number of human pathologies including Alzheimer's disease. As discussed in detail below, we have solved the structure of a ten residue VQIINK (SEQ ID NO: 11) peptide and discovered that it forms an extensive steric zipper interface that buries twice the surface area of VQIVYK (SEQ ID NO: 9), a discovery that provides evidence that this sequence is a dominating factor that drives Tau fibrillization and an ideal inhibitor target. Building upon this discovery, we found that engineered constructs containing only VQIINK (SEQ ID NO: 11) exhibit accelerated aggregation compared to wild-type, whereas those containing only VQIVYK (SEQ ID NO: 9) aggregate more slowly and allow a mixture of oligomeric and fibrillar species to form. Additionally, the VQIINK (SEQ ID NO: 11) structure reported herein rationalizes how the disease associated mutant ΔK280 could enhance Tau fiber formation, and a second VQIINK (SEQ ID NO: 11) structure of an alternative polymorph explains how different Tau strains could assemble. We then discovered that certain capping inhibitors designed to target VQIINK (SEQ ID NO: 11) based on these structures reduce full-length Tau fibrillization in vitro and block seeding by full-length Tau fibrils in HEK293 biosensor cells.

The VQIINK (SEQ ID NO: 11) crystal structures disclosed herein provided the crucial tools that allowed the structure-based inhibitor design and development of new compositions comprising these sequences. In this context, embodiments of the invention include compositions of matter comprising a peptide comprising at least one amino acid substitution in the amino acid sequence KVQIINKKLD (SEQ ID NO: 1), wherein the amino acid substitution(s) is/are at residue K1, Q3, I4, I5, N6, L9 or D10; and a pharmaceutically acceptable carrier including a peptide stabilizing excipient. In illustrative embodiments of the invention, the peptide comprises the amino acid sequence DVQMINKKRK (SEQ ID NO: 2), DVQWINKKRK (SEQ ID NO: 3), DVQRINKKRK (SEQ ID NO: 4), DVWMINKKRK (SEQ ID NO: 5), NKKRK (SEQ ID NO: 6), DVWMWNKKRK (SEQ ID NO: 7), DVWWWUN-KKRK (SEQ ID NO: 8), or VQIVYK (SEQ ID NO: 9). In typical embodiments of the invention, the peptide stabilizing excipient within the composition comprises a preservative, a tonicity adjusting agent, a detergent, a hydrogel, a viscosity adjusting agent, or a pH adjusting agent.

In certain compositions of the invention, the peptide is coupled to a plurality of heterologous amino acids. For example, in some embodiments of the invention, the peptide is fused, optionally via a linker sequence, to a plurality of heterologous amino acids comprising a cell penetrating peptide (CPP). Optionally, the plurality of heterologous amino acids (e.g. a CPP) is less than 30 amino acids in length. In certain embodiments of the invention, the CPP comprises a plurality of arginine residues, for example 4 to 16 contiguous arginine residues. In some embodiments of the invention, the peptide comprises a non-naturally occurring amino acid such as a D amino acid.

In some embodiments of the invention, the composition comprises a cocktail of different peptide inhibitors such as a first peptide comprising at least one amino acid substitution in the amino acid sequence KVQIINKKLD (SEQ ID NO: 1), wherein the amino acid substitution is at residue K1, Q3, 14, 15, N6, L9 or D10; in combination with a second peptide comprising at least one amino acid substitution in the amino acid sequence KVQIINKKLD (SEQ ID NO: 1), wherein the amino acid substitution is at residue K1, Q3, 14, 15, N6, L9 or D10. In an illustrative embodiment of the invention, the composition comprises a first peptide having the amino acid sequence VQIVYK (SEQ ID NO: 9), and a second peptide having the amino acid sequence VQIINK (SEQ ID NO: 11), wherein relative amounts of the first and second peptide within the composition effect the ability of the composition to inhibit aggregation of a specific Tau isoform.

Another embodiment of the invention is a method for treating a subject having an amyloid disease characterized by aggregation of Tau protein, the method comprising administering to the subject an effective amount of a pharmaceutical composition comprising a peptide comprising at least one amino acid substitution in the amino acid sequence KVQIINKKLD (SEQ ID NO: 1), wherein the amino acid substitution is at residue K1, Q3, 14, IS, N6, L9 or D10, and a pharmaceutically acceptable carrier including a peptide stabilizing excipient. In illustrative embodiments of the invention, the peptide used in this method comprises the amino acid sequence DVQMINKKRK (SEQ ID NO: 2), DVQWINKKRK (SEQ ID NO: 3), DVQRINKKRK (SEQ ID NO: 4), DVWMINKKRK (SEQ ID NO: 5), D NKKRK (SEQ ID NO: 6), DVWMWNKKRK (SEQ ID NO: 7), D KKRK (SEQ ID NO: 8), or VQIVYK (SEQ ID NO: 9). In certain embodiments of these methods, the amyloid disease characterized by aggregation of Tau protein is Alzheimer's disease.

A related embodiment of the invention is a method of inhibiting formation of Tau fibrils comprising combining Tau with a composition comprising a peptide having at least one amino acid substitution in the amino acid sequence KVQIINKKLD (SEQ ID NO: 1), wherein the amino acid substitution is at residue K1, Q3, 14, 15, N6, L9 or D10. In this method, the peptide is then allowed to interact with Tau so that Tau fibril formation is inhibited. Optionally in these embodiments of the invention, the composition comprises a cocktail of different peptide inhibitors such as a first peptide comprising at least one amino acid substitution in the amino acid sequence KVQIINKKLD (SEQ ID NO: 1), wherein the amino acid substitution is at residue K1, Q3, 14, 15, N6, L9 or D10; in combination with a second peptide comprising at least one amino acid substitution in the amino acid sequence KVQIINKKLD (SEQ ID NO: 1), wherein the amino acid substitution is at residue K1, Q3, 14, 15, N6, L9 or D10. In typical embodiments of the invention the peptide is selected for its ability to inhibit the formation of Tau fibrils by inhibiting Tau protein seeding. In certain embodiments of the invention, the peptide is combined with Tau in vivo so as to inhibit the development or progression of a tauopathy in an individual, such as a patient suffering from Alzheimer's disease.

Other objects, features and advantages of the present invention will become apparent to those skilled in the art from the following detailed description. It is to be understood, however, that the detailed description and specific examples, while indicating some embodiments of the present invention, are given by way of illustration and not limitation. Many changes and modifications within the scope of the present invention may be made without departing from the spirit thereof, and the invention includes all such modifications.

DETAILED DESCRIPTION OF THE INVENTION

Figure 1A:
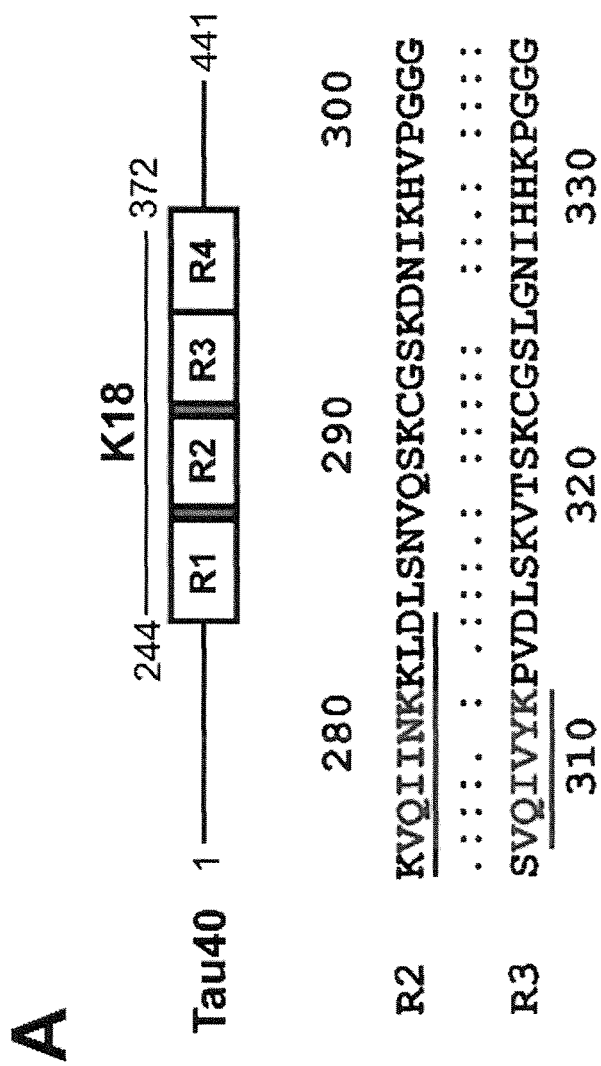
FIG. 1 Atomic structures of amyloid fibrils formed by segments of Tau, viewed down the fibril axes. (A) Schematic of full-length Tau showing the positions of VQIINK (SEQ ID NO: 11) and VQIVYK (SEQ ID NO: 9) (colored red) in the microtubule binding domain which contains four repeats (R1-4) together termed K18. Shown below is a sequence alignment of Repeats 2 and 3 (R2 and R3) from human Tau with the VQIINK (SEQ ID NO: 11) and VQIVYK (SEQ ID NO: 9) segments underlined. (B) Comparison of buried surface area $A_b$ and shape complementarity S, for the VQIINK (SEQ ID NO: 11) (interface A; this paper) and VQIVYK (SEQ ID NO: 9) (Sawaya et al. 2007; PBD 2ON9) steric zippers. (C) The two steric zipper interfaces, A and B, in the ten residue KVQIINKKLD (SEQ ID NO: 1) crystal, shown as stick models with superimposed van der Waals atomic radii. The two interfaces have similar buried areas and shape complementarities. Numbering in C corresponds to the N- and C-termini for the β-sheet colored in cyan. (D) Arrangement of interfaces A and B in the ten residue wild-type KVQIINKKLD (SEQ ID NO: 1) structure (left) and the predicted arrangement in the ΔK280 mutant (center and right). Trapezoids in the center diagram represent steric zipper forming residues that that are predicted to line the interface between the mated β-strands. The colored arrows show the directions of β-strands forming the steric zippers. Oxygen atoms are red; nitrogen atoms are blue, and main-chain atoms are green for Chains A and C, and cyan for Chain B. In the wild-type structure, interfaces A (red) and B (blue) are formed on opposite faces of the VQIINK (SEQ ID NO: 11) β-sheet. Deletion of residue K280 is predicted to reverse the orientation of C-terminal residues by 180° about the β-strand axes (center) merging steric zipper interfaces A and B into a single extended steric zipper interface with greater $A_b$ and $S_c$ as calculated from the ΔK280 model (right and Inset 1).

In the description of embodiments, reference may be made to the accompanying figures which form a part hereof, and in which is shown by way of illustration a specific embodiment in which the invention may be practiced. It is to be understood that other embodiments may be utilized and structural changes may be made without departing from the scope of the present invention. Many of the techniques and procedures described or referenced herein are well understood and commonly employed by those skilled in the art. Unless otherwise defined, all terms of art, notations and other scientific terms or terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art.

As discussed in detail below, we have solved the structure of a ten residue VQIINK (SEQ ID NO: 11) peptide and discovered that it forms an extensive steric zipper interface that buries twice the surface area of VQIVYK (SEQ ID NO: 9), a discovery that provides evidence that this sequence is a dominating factor that drives Tau fibrillization and an ideal inhibitor target. Building upon this discovery, we found that engineered constructs containing only VQIINK (SEQ ID NO: 11) exhibit accelerated aggregation compared to wild-type, whereas those containing only VQIVYK (SEQ ID NO: 9) aggregate more slowly and allow a mixture of oligomeric and fibrillar species to form. The VQIINK (SEQ ID NO: 11) crystal structures disclosed herein provide crucial tools that allow structure-based inhibitor design and development of new compositions comprising these sequences.

Embodiments of the Tau VQIINK (SEQ ID NO: 11) inhibitors disclosed herein can be utilized to establish the role played by Tau aggregates in pathogenicity associated with Alzheimer's disease and other tauopathies using animal models. Embodiments of the Tau VQIINK (SEQ ID NO: 11) inhibitors disclosed herein may also be used to block the formation of pathological Tau aggregates associated in human disease. In addition, embodiments of the Tau VQIINK (SEQ ID NO: 11) inhibitors disclosed herein can be used to probe Tau assemblies including different pathological strains and soluble oligomers to uncover details about the underlying molecular structure.

Inhibitors designed from atomic resolution structures of VQIINK (SEQ ID NO: 11) amyloids function by targeting the VQIINK (SEQ ID NO: 11) motif in the full-length protein and introduce bulky residues into interfaces of the VQIINK (SEQ ID NO: 11) amyloid structure that are critical for amyloid fiber growth. In this way, the designed inhibitors are capable of inhibiting or reversing Tau aggregation. In addition, VQIINK (SEQ ID NO: 11) inhibitors can be added to Tau monomer to prevent amyloid fiber formation, or added to existing Tau fibers to prevent growth and seeding.

An advantage that the VQIINK (SEQ ID NO: 11) inhibitors disclosed herein have over existing Tau capping inhibitors that target only VQIVYK (SEQ ID NO: 9) is that they target VQIINK (SEQ ID NO: 11), which we show is a more potent inducer of Tau aggregation. This allows VQIINK (SEQ ID NO: 11) inhibitors to block full-length Tau aggregation more effectively. Also, combining the VQIINK (SEQ ID NO: 11) inhibitors with existing VQIVYK (SEQ ID NO: 9) inhibitors allows both sites in full-length Tau to be targeted, thus improving the potency of the existing VQIVYK (SEQ ID NO: 9) inhibitors.

The state of the related art prior to the invention is illustrated in Sievers, S. A. et al. Structure-based design of non-natural amino-acid inhibitors of amyloid fibril formation. Nature 475, 96-100, (2011), which showed that capping inhibitors targeting the VQIVYK (SEQ ID NO: 9) amyloid structure could block the aggregation of Tau isoforms that lacked VQIINK (SEQ ID NO: 11). In this publication, the structure of one of the two fiber-forming segments in Tau, VQIVYK (SEQ ID NO: 9) was determined, and from it capping inhibitors were designed to block the aggregation of Tau by inhibiting VQIVYK (SEQ ID NO: 9) amyloid formation. The inhibitors worked well on Tau isoforms that contained only VQIVYK (SEQ ID NO: 9), but were not as effective at blocking full-length Tau aggregation and seeding, as the full-length protein also contains a VQIINK (SEQ ID NO: 11) fibrillization site.

Using MicroED[12-14] we determined structures of fibrils containing VQIINK (SEQ ID NO: 11) by electron diffraction. We determined the precise structure of VQIINK (SEQ ID NO: 11) and further designed inhibitors that target the VQIINK (SEQ ID NO: 11) segment, which we show to be a potent stimulator of Tau amyloid fiber formation. Insights from these structures allowed us to design VQIINK (SEQ ID NO: 11) inhibitors that block full-length Tau aggregation in vitro, and also to block seeding in HEK293 biosensor cells. These structures, coupled with biochemical experiments, provide evidence on the relative contributions of VQIINK (SEQ ID NO: 11) and VQIVYK (SEQ ID NO: 9) to Tau aggregation, and offer insights into Tau fibril polymorphism and the phenomenon of Tau strains.

As discussed in detail below, there are a number of embodiments of the invention based upon the inventors' discoveries. Embodiments of the invention include compositions of matter comprising a VQIINK (SEQ ID NO: 11) peptide inhibitor, for example a peptide having at least one amino acid substitution in the amino acid sequence KVQIINKKLD (SEQ ID NO: 1), wherein the amino acid substitution is at residue K1, Q3, 14, 15, N6, L9 or D10. Typically, the peptide is combined with a pharmaceutically acceptable carrier including a peptide stabilizing excipient (i.e. an agent that stabilizes the structure of the peptide or facilitates the delivery of the peptide to an in vivo environment). In illustrative embodiments of the invention, the peptide comprises the amino acid sequence DVQMINKKRK (SEQ ID NO: 2), DVQWINKKRK (SEQ ID NO: 3), DVQRINKKRK (SEQ ID NO: 4), DVWMINKKRK (SEQ ID NO: 5), D NKKRK (SEQ ID NO: 6), DVWMWNKKRK (SEQ ID NO: 7), DVWWWUNKKRK (SEQ ID NO: 8), or VQIVYK (SEQ ID NO: 9). In illustrative embodiments of the invention, the peptide stabilizing excipient within the composition comprises a preservative, a tonicity adjusting agent, a detergent, a hydrogel, a viscosity adjusting agent, or a pH adjusting agent.

In certain compositions of the invention, the peptide is coupled to a plurality of heterologous amino acids. For example, in some embodiments of the invention, the peptide is fused, optionally via a linker sequence (e.g. 1-7 amino acids), to a plurality of heterologous amino acids comprising a cell penetrating peptide (CPP). Optionally, the plurality of heterologous amino acids (e.g. a CPP) is less than 30 amino acids in length. In certain embodiments of the invention, the CPP comprises a plurality of arginine residues, for example 4 to 16 contiguous arginine residues. In some embodiments of the invention, the peptide comprises a non-naturally occurring amino acid such as a D amino acid.

In some embodiments of the invention, the composition comprises a cocktail of different peptide inhibitors such as a first peptide comprising at least one amino acid substitution in the amino acid sequence KVQIINKKLD (SEQ ID NO: 1), wherein the amino acid substitution is at residue K1, Q3, 14, IS, N6, L9 or D10; in combination with a second peptide comprising at least one amino acid substitution in the amino acid sequence KVQIINKKLD (SEQ ID NO: 1), wherein the amino acid substitution is at residue K1, Q3, 14, IS, N6, L9 or D10. In an illustrative embodiment of the invention, the composition comprises a first peptide having the amino acid sequence VQIVYK (SEQ ID NO: 9), and a second peptide having the amino acid sequence VQIINK (SEQ ID NO: 11), wherein relative amounts of the first and second peptide within the composition effect the ability of the composition to inhibit aggregation of a specific Tau iso form.

Another embodiment of the invention is a method for treating a subject having an amyloid disease characterized by aggregation of Tau protein, comprising administering to the subject an effective amount of a pharmaceutical composition comprising a peptide comprising at least one amino acid substitution in the amino acid sequence KVQIINKKLD (SEQ ID NO: 1), wherein the amino acid substitution is at residue K1, Q3, 14, 15, N6, L9 or D10, and a pharmaceutically acceptable carrier including a peptide stabilizing excipient. In illustrative embodiments of the invention, the peptide comprises the amino acid sequence DVQMINKKRK (SEQ ID NO: 2), DVQWINKKRK (SEQ ID NO: 3), DVQRINKKRK (SEQ ID NO: 4), DVWMINKKRK (SEQ ID NO: 5), NKKRK (SEQ ID NO: 6), DVWMWNKKRK (SEQ ID NO: 7), DVWWWUNKKRK (SEQ ID NO: 8), or VQIVYK (SEQ ID NO: 9). In certain embodiments of these methods, the amyloid disease characterized by aggregation of Tau protein is Alzheimer's disease.

A related embodiment of the invention is a method of inhibiting formation of Tau fibrils comprising combining Tau with a composition comprising a peptide having at least one amino acid substitution in the amino acid sequence KVQIINKKLD (SEQ ID NO: 1), wherein the amino acid substitution is at residue K1, Q3, 14, IS, N6, L9 or D10. In this method, the peptide is then allowed to interact with Tau so that Tau fibril formation is inhibited. Optionally in these embodiments of the invention, the composition comprises a cocktail of different peptide inhibitors such as a first peptide comprising at least one amino acid substitution in the amino acid sequence KVQIINKKLD (SEQ ID NO: 1), wherein the amino acid substitution is at residue K1, Q3, 14, IS, N6, L9 or D10; in combination with a second peptide comprising at least one amino acid substitution in the amino acid sequence KVQIINKKLD (SEQ ID NO: 1), wherein the amino acid substitution is at residue K1, Q3, 14, IS, N6, L9 or D10. In typical embodiments of the invention the peptide is selected for its ability to inhibit the formation of Tau fibrils by inhibiting Tau protein seeding. In certain embodiments of the invention, the peptide is combined with Tau in vivo so as to inhibit the development or progression of a tauopathy in an individual, such as a patient suffering from Alzheimer's disease.

Another illustrative embodiment of the invention is a composition of matter comprising a peptide having the amino acid sequence VQIINK (SEQ ID NO: 11) (and/or VQIVYK, (SEQ ID NO: 9)) and a pharmaceutically acceptable carrier including a peptide stabilizing excipient. Embodiments also include a composition of matter comprising a first peptide having the amino acid sequence VQIVYK (SEQ ID NO: 9), a second peptide having the amino acid sequence VQIINK (SEQ ID NO: 11), and a pharmaceutically acceptable carrier including a peptide stabilizing excipient, wherein relative amounts of the first and second peptide within the composition are controlled/defined so as to affect the ability of the composition to inhibit aggregation of a specific Tau isoform. Typically, the peptide stabilizing excipient is a preservative that inhibits the growth of microorganisms.

As discussed in detail below, embodiments of the invention include, e.g., to inhibitory peptides; molecules in which a VQIINK (SEQ ID NO: 11) and/or VQIVYK (SEQ ID NO: 9) peptides of the invention is fused to a cell penetrating peptide (CPP), which fusion molecules are sometimes referred to herein as "CPP inhibitors"; pharmaceutical compositions comprising an inhibitory peptide or a CPP inhibitor of the invention and a pharmaceutically acceptable carrier; methods of using the inhibitory peptides or the CPP inhibitors to restore the structure and function of Tau molecules having an aberrant conformation, e.g. (a) to block or inhibit Tau aggregation (e.g., to delay the onset of aggregation and/or to lower the amount of aggregates, in solution, in a cell, or in a subject having a pathology that comprises Tau aggregates) and/or (b) to restore the folding of a misfolded Tau, thereby re-activating a biological or biochemical activity of Tau due to the aberrant conformation; methods for treating a subject having a pathology which comprises aggregated Tau (e.g., either wild type or mutant aggregated Tau), comprising administering to the subject or contacting the aggregate with an effective amount of a CPP inhibitor of the invention.

As noted above, in certain embodiments of the invention, an inhibitory peptide disclosed herein is coupled to heterologous amino acids such as a cell penetrating peptide (CPP) amino acid sequence, typically one less than 30 amino acids in length. Optionally the peptide is coupled to the CPP by a peptide linker comprising 1-7 amino acids. In some embodiments of the invention, the CPP forms a polycationic structure. In other embodiments of the invention, the CPP forms an amphipathic structure. Embodiments of the invention include peptides wherein the peptide comprises at least on D amino acid. Embodiments of the invention can further compare metabolic stability and efficacy of L- and D form peptide inhibitors.

Embodiments of the invention can further be used to develop strain-selective VQIINK (SEQ ID NO: 11) inhibitors (or combinations such as VQIINK (SEQ ID NO: 11) inhibitors combined with VQIVYK (SEQ ID NO: 9) inhibitors) based on information from the crystal structures and inhibitor scaffolds reported herein for use in chemical biology studies to classify Tau strains from pathological aggregates with specific morphologies according their inhibitor class sensitivities. Additionally, soluble Tau oligomers will be scrutinized with these inhibitors to determine from what molecular structures they arise, and whether they are comprised of a beta structure that resembles the amyloid fiber. In some embodiments of the invention, the VQIINK (SEQ ID NO: 11) inhibitor (and optionally cell-penetrating) peptide sequences will be introduced into full-length Tau and truncated forms to harness Tau's natural blood brain barrier penetrability to facilitate delivery of inhibitor molecules to the brain.

An inhibitory peptide or CPP inhibitor of the invention can be synthesized (e.g., chemically or by recombinant expression in a suitable host cell) by any of a variety of art-recognized methods. In order to generate sufficient quantities of an inhibitory peptide for use in a method of the invention, a practitioner can, for example, using conventional techniques, generate nucleic acid (e.g., DNA) encoding the peptide and insert it into an expression vector, in which the sequence is under the control of an expression control sequence such as a promoter or an enhancer, which can then direct the synthesis of the peptide. For example, one can (a) synthesize the DNA de novo, with suitable linkers at the ends to clone it into the vector; (b) clone the entire DNA sequence into the vector; or (c) starting with overlapping oligonucleotides, join them by conventional PCR-based gene synthesis methods and insert the resulting DNA into the vector. Suitable expression vectors (e.g., plasmid vectors, viral, including phage, vectors, artificial vectors, yeast vectors, eukaryotic vectors, etc.) will be evident to skilled workers, as will methods for making the vectors, inserting sequences of interest, expressing the proteins encoded by the nucleic acid, and isolating or purifying the expressed proteins. In illustrative embodiments of the invention, capping inhibitor peptides are loaded into adeno-associated virus (AAV) capsids and hydrogel-based polymers to mediate delivery across the blood brain barrier One aspect of the invention is a method for reducing or inhibiting Tau aggregation, comprising contacting Tau amyloid protofilaments with an effective amount of one or more of the inhibitory peptides or CPP inhibitors of the invention. Such a method can be carried out in vitro (in solution) or in vivo (e.g. cells in culture or in a subject). Another aspect of the invention is a method for restoring the conformation of a Tau protein molecule having an aberrant conformation. An "aberrant conformation," as used herein, refers to a conformation which is different from the wild type conformation, and which results in a loss of function of the molecule. Such aberrant conformation is sometimes referred to herein as pathological conformation. The aberrant conformation can take the form of amyloid aggregates or fibers (fibrils) of Tau molecules with other Tau molecules or with other proteins. Alternatively, the aberrant conformation can take the form of misfolding (e.g., partial or complete unfolding) of the Tau protein due to mutations or other factors. In this method for restoring the conformation of a Tau protein having an aberrant conformation, the Tau molecule having the aberrant conformation is contacted with an effective amount of an inhibitory peptide or a CPP inhibitor of the invention. The contacted Tau molecule has a restored conformation, and exhibits a restored or reactivated biological or biochemical activity.

Another aspect of the invention is a method for reactivating or restoring a biological or biochemical activity (function) of a Tau protein which results from aberrant conformation of the Tau protein. The method comprises contacting the Tau protein molecule having an aberrant conformation with an effective amount of an inhibitor peptide or CPP inhibitor of the invention. As a result of contacting the Tau protein having the aberrant conformation, the lost biological or biochemical activity of the Tau molecule is reactivated or restored.

Another aspect of the invention is a method for inhibiting or preventing a loss of a biological or biochemical activity (function), of a Tau protein which results from aberrant conformation of the Tau protein. The method comprises contacting the Tau protein molecule having an aberrant conformation with an effective amount of an inhibitor peptide or CPP inhibitor of the invention. As a result of contacting the Tau protein having the aberrant conformation, the loss of activity of the Tau molecule is inhibited or prevented.

Another aspect of the invention is a method for treating a subject having a disease or condition which is mediated by loss of function of Tau, such as a pathological syndrome in which Tau has an abnormal conformation (e.g. is aggregated or misfolded). That is, the pathological syndrome is associated with Tau having an aberrant conformation. The method comprises administering to the subject an effective amount of one or more CPPs of the invention. In some embodiments, a cocktail of two of more of the peptides or CPP inhibitor peptides is used.

Yet another embodiment of the invention is a method of observing the presence or absence of Tau amyloid fibrils in a biological sample comprising combining a biological sample with a peptide disclosed herein that binds to Tau, allowing the peptide to bind to Tau amyloid fibrils that may be present in the biological sample, and then monitoring this combination for the presence of complexes formed between Tau amyloid fibrils and the peptide; wherein the presence of said complexes show the presence of Tau amyloid fibrils in the biological sample. Optionally in this method, the presence of complexes formed between Tau amyloid fibrils and the peptide is monitored using a detectable label that is coupled to the peptide (e.g. a heterologous peptide tag). Typically, the method is performed on a biological sample obtained from an individual suspected of suffering from a tauopathy. Such embodiments of the invention can be used, for example, in diagnostic methods designed to observe the presence or status of Alzheimer's disease, for example to detect disease beginnings before clinical symptoms, and to follow the effectiveness (or lack of effectiveness), of a therapeutic treatment.

Peptide inhibitors of the invention bind specifically (selectively, preferentially) to Tau rather than to unintended proteins. The protein to which the peptide inhibitor binds may be, e.g., a monomer, small aggregate, oligomer, or fibril. For example, the binding can be 2 times, 5 times, 10 times, 100 times or 200 times stronger, or no binding at all can be detected to an unintended target. Conventional methods can be used to determine the specificity of binding, such as e.g. competitive binding assays or other suitable analytic methods.

Active variants of the inhibitory peptides described above are also included. An "active variant" is a variant which retains at least one of the properties of the inhibitory peptides described herein (e.g., the ability to bind to Tau and/or to block, inhibit or prevent Tau fibrillation (aggregation) and/or Tau cytotoxicity). Fibrilization, as used herein, refers to the formation of fiber or fibrils, such as amyloid fibrils.

Suitable active variants include peptidomimetic compounds (any compound containing non-peptidic structural elements that is capable of mimicking the biochemical and/or biological action(s) of a natural mimicked peptide), including, for example, those designed to mimic the structure and/or binding activity (such as, for example, hydrogen bonds and hydrophobic packing interactions) of the peptides according to the methods disclosed herein). Inhibitory peptides of the invention, including active variants thereof, are sometimes referred to herein as "peptidic compounds" or "compounds."

In one embodiment, active variants of the inhibitory peptides are shortened by 1-3 (e.g., 1, 2 or 3) amino acids at either the N-terminus, the C-terminus, or both of the starting inhibitory peptide. In another embodiment, the active variants are lengthened (extended) by 1, 2, 3 or 4 amino acids at the C-terminal end of the starting inhibitory peptide, e.g. with amino acid residues at the position in which they occur in Tau.

A variety of other types of active variants are included in embodiments of the invention. In some embodiments, amino acids other than the ones noted above are substituted. These amino acids can help protect the peptide inhibitors against proteolysis or otherwise stabilize the peptides, and/or contribute to desirable pharmacodynamic properties in other ways. In some embodiments, the non-natural amino acids allow an inhibitor to bind more tightly to the target because the side chains optimize hydrogen bonding and/or apolar interactions with it. In addition, non-natural amino acids offer the opportunity of introducing detectable markers, such as strongly fluorescent markers which can be used, e.g., to measure values such as inhibition constants. Also included are peptide mimetics, such as, e.g., peptoids, beta amino acids, N-ethylated amino acids, and small molecule mimetics.

In one embodiment, non-natural amino acids are substituted for amino acids in the sequence. More than 100 non-natural amino acids are commercially available. These include, for example, Non-Natural Amino Acids which can Substitute for LEU:

| L-cyclohexylglycine | 161321-36-4 |
| L-phenylglycine | 102410-65-1 |
| 4-hydroxy-D-phenylglycine | 178119-93-2 |
| L-α-t-butylglycine | 132684-60-7 |
| cyclopentyl-Gly-OH | 220497-61-0\ |

Non-Natural Amino Acids which can Substitute for THR:

| Thr(tBu)-OH | 71989-35-0 |
| (RS)-2-amino-3-hydroxy-3-methylbutanoic acid | 105504-72-1 |

Non-Natural Amino Acids which can Substitute for ILE:

| allo-Ile-OH | 251316-98-0 |
| N-Me-allo-Ile-OH | 136092-80-3 |
| Homoleu-OH | 180414-94-2 |

Non-Natural Amino Acids which can Substitute for ARG:

| Nω-nitro-L-arginine | 58111-94-7 |
| L-citrulline | 133174-15-9 |

Non-Natural Amino Acids which can Substitute for TYR:

| 3-amino-L-tyrosine | 726181-70-0 |
| 3-nitro-L-tyrosine | 136590-09-5 |
| 3-methoxy-L-tyrosine | |
| 3-iodo-L-tyrosine | 134486-00-3 |
| 3-chloro-L-tyrosine | 478183-58-3 |
| 3,5-dibrimo-L-tyrosine | 201484-26-6 |

Non-Natural Amino Acids which can Substitute for LYS:

| Lys(retro-Abz-)-OH | 159322-59-5 |
| Lys(Mca)-OH | 386213-32-7 |
| (Nδ-4-methyltrityl)-L-ornithine | 343770-23-0 |
| N-α--N-ε-(d-Biotin)-L-lysine | 146987-10-2 |

In another embodiment, one or more (e.g. 1, 2, 3, 4, 5, 6, 7, 8, 9 or 10) of the L-amino acids are substituted with a D amino acid. In another embodiment, one or more (e.g. 1, 2, 3, 4, 5, 6, 7, 8, 9 or 10) N-methylated residues are included in the peptide. An inhibitory peptide of the invention can comprise, e.g., L-amino acids, D-amino acids, other non-natural amino acids, or combinations thereof.

Active variants include molecules comprising various tags at the N-terminus or the C-terminus of the peptide (e.g. tags comprising a stretch of heterologous amino acids). For example, an inhibitory peptide of the invention can comprise as tags at its N-terminus and/or at its C-terminus: 1, 2, 3, 4, 5, 6, 7, 8, 9 or 10 or more Lysine residues; 1, 2, 3, 4, 5, 6, 7, 8, 9 or 10 or more Arginine residues; 1, 2, 3, 4, 5, 6, 7, 8, 9 or 10 or more Glutamate residues; 1, 2, 3, 4, 5, 6, 7, 8, 9 or 10 or more Aspartate residues; combinations of these amino acid residues; or other polar tags that will be evident to a skilled worker. Other active variants include mutations of the Tau sequence which increase affinity of the inhibitory peptides for the Tau.

In one embodiment of the invention, an inhibitory peptide of the invention is isolated or purified, using conventional techniques such as the methods described herein. By "isolated" is meant separated from components with which it is normally associated, e.g., components present after the peptide is synthesized. An isolated peptide can be a cleavage product of a protein which contains the peptide sequence. A "purified" inhibitory peptide can be, e.g., greater than 90%, 95%, 98% or 99% pure.

In one embodiment, to enhance the cell permeability of an inhibitory peptide of the invention, the peptide is fused to any of a variety of cell penetrating peptides (CPPs). CPPs typically have an amino acid composition that either contains a high relative abundance of positively charged amino acids such as lysine or arginine or has sequences that contain an alternating pattern of polar/charged amino acids and non-polar, hydrophobic amino acids. These two types of structures are referred to as polycationic or amphipathic, respectively. A third class of CPP's are the hydrophobic peptides, containing only apolar residues, with low net charge or have hydrophobic amino acid groups that are crucial for cellular uptake. Some typical CPP's that can be fused to an inhibitory peptide of the invention are provided in Table 1 below.

TABLE 1

| Name | Sequence |
| --- | --- |
| polyARG | nR where 4 < n < 17 (e.g., n = 5, 6, 7, 8, 9, 10, 11, 12, 13, 14, 15 or 16) (SEQ ID NO: 13) |
| polyLYS | nK where 4 < K < 17 (e.g., K = 5, 6, 7, 8, 9, 10, 11, 12, 13, 14, 15 or 16) |
| D-polyARG | nR where 4 < n < 17 (e.g., n = 5, 6, 7, 8, 9, 10, 11, 12, 13, 14, 15 or 16) |
| D-polyLYS | nK where 4 < K < 17 (e.g., K = 5, 6, 7, 8, 9, 10, 11, 12, 13, 14, 15 or 16) |
| SynB1 | RGGRLSYSRRRFSTSTGR (SEQ ID NO: 14) |
| SynB3 | RRLSYSRRRF (SEQ ID NO: 15) |
| Penetratin | RQIKIWFQNRRMKWKK (SEQ ID NO: 16) |
| PenArg | RQIRIWFQNRRMRWRR (SEQ ID NO: 17) |
| PenLys | KQIKIWFQNKKMKWKK (SEQ ID NO: 18) |
| TatP59W | GRKKRRQRRRPWQ (SEQ ID NO: 19) |
| Tat (48-60) | GRKKRRQRRRPPQ (SEQ ID NO: 20) |
| R9-Tat | GRRRRRRRRPPQ (SEQ ID NO: 21) |
| Tat | YGRKKRRQRRR (SEQ ID NO: 22) |
| D-Tat | GRKKRRQRRRPPQ (SEQ ID NO: 23). |
| BMVGag (7-25) | KMTRAQRRAAARRNRWTAR (SEQ ID NO: 24) |

Other representative CPPs useful in embodiments of the invention are found, for example in WO 2018/005867, the contents of which are incorporated herein by refernce.

In typical embodiments of the invention, the CPP comprises a plurality of arginine residues (e.g. $R_{1-16}$). In general, it is advisable that the length of the CPP is rather short, e.g. less than about 30 amino acids, in order to improve stability and pharmacodynamic properties once the molecule enters a cell. In some embodiments, the CPP is directly attached (fused) to a peptide of the invention. In other embodiments, it is desirable to separate the highly charged CPP from the inhibitor peptide with a linker, to allow the inhibitor to retain its activity. Any of a variety of linkers can be used. The size of the linker can range, e.g., from 1-7 or even more amino acids (e.g., 1, 2, 3, 4, 5, 6 or 7 amino acids).

In embodiments of the invention, the inhibitory peptide can be detectably labeled. Labeled peptides can be used, e.g., to better understand the mechanism of action and/or the cellular location of the inhibitory peptide. Suitable labels which enable detection (e.g., provide a detectable signal, or can be detected) are conventional and well-known to those of skill in the art. Suitable detectable labels include, e.g., radioactive active agents, fluorescent labels, and the like. Methods for attaching such labels to a protein, or assays for detecting their presence and/or amount, are conventional and well-known.

An inhibitory peptide of the invention can be synthesized (e.g., chemically or by recombinant expression in a suitable host cell) by any of a variety of art-recognized methods. In order to generate sufficient quantities of an inhibitory peptide for use in a method of the invention, a practitioner can, for example, using conventional techniques, generate nucleic acid (e.g., DNA) encoding the peptide and insert it into an expression vector, in which the sequence is under the control of an expression control sequence such as a promoter or an enhancer, which can then direct the synthesis of the peptide. For example, one can (a) synthesize the DNA de novo, with suitable linkers at the ends to clone it into the vector; (b) clone the entire DNA sequence into the vector; or (c) starting with overlapping oligonucleotides, join them by conventional PCR-based gene synthesis methods and insert the resulting DNA into the vector. Suitable expression vectors (e.g., plasmid vectors, viral, including phage, vectors, artificial vectors, yeast vectors, eukaryotic vectors, etc.) will be evident to skilled workers, as will methods for making the vectors, inserting sequences of interest, expressing the proteins encoded by the nucleic acid, and isolating or purifying the expressed proteins.

Another aspect of the invention is a pharmaceutical composition comprising one or more of the inhibitory peptides and a pharmaceutically acceptable carrier. Optionally, the components of the pharmaceutical composition can be detectably labeled, e.g. with a radioactive or fluorescent label, or with a label, for example one that is suitable for detection by positron emission spectroscopy (PET) or magnetic resonance imaging (MRI). For example, peptides of the invention can be coupled to a detectable label selected from the group consisting of a radioactive label, a radioopaque label, a fluorescent dye, a fluorescent protein, a colorimetric label, and the like. In some embodiments, the inhibitory peptide is present in an effective amount for the desired purpose. The compositions may contain preservatives and/or antimicrobial agents as well as pharmaceutically acceptable auxiliary substances as required to approximate physiological conditions, such as pH adjusting and buffering agents, tonicity adjusting agents, wetting agents, detergents and the like.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use. For example, "pharmaceutically acceptable salts" of a compound means salts that are pharmaceutically acceptable, as defined herein, and that possess the desired pharmacological activity of the parent compound.

Another aspect of the invention is a polynucleotide encoding an inhibitory peptide of the invention. In embodiments of the invention, the polynucleotide is operably linked to a regulatory control sequence (e.g., a promoter or an enhancer) to facilitate production of the encoded protein following introduction (e.g. by transfection) into a suitable cell. Other embodiments include a cell comprising the expression vector; and a method of making an inhibitory peptide of the invention comprising cultivating the cell and harvesting the peptide thus generated.

Another aspect of the invention is a kit for carrying out any of the methods described herein. The kit may comprise a suitable amount of an inhibitory peptide of the invention; reagents for generating the peptide; reagents for assays to measure their functions or activities; or the like. Kits of the invention may comprise instructions for performing a method. Other optional elements of a kit of the invention include suitable buffers, media components, or the like; a computer or computer-readable medium providing the structural representation of a crystal structure described herein; containers; or packaging materials. Reagents for performing suitable controls may also be included. The reagents of the kit can be in containers in which the reagents are stable, e.g., in lyophilized form or stabilized liquids. The reagents may also be in single use form, e.g., in single reaction form for administering to a subject.

Characterization of candidate inhibitory peptides of the invention can be carried out by any of a variety of conventional methods. For example, the peptides can be assayed for the ability to reduce or inhibit Tau aggregation or cytotoxicity or cell-to-cell spread. The assays can be carried out in vitro or in vivo. Suitable assays will be evident to a skilled worker; some suitable assays are described herein.

One aspect of the invention is a method for reducing or inhibiting Tau aggregation, comprising contacting Tau protofilaments with an effective amount of one or more of the inhibitory peptides of the invention. Such a method can be carried out in solution or in a cell (e.g. cells in culture or in a subject).

Another aspect of the invention is a method for treating a subject having a disease or condition which is mediated by the presence of fibrillated Tau (sometimes referred to herein as a Tauopathy or a Tau-mediated disease or condition), comprising administering to the subject an effective amount of an inhibitory peptide or pharmaceutical composition of the invention. Among such diseases or conditions are, e.g., Alzheimer's disease. Another aspect of the invention is a method to prevent the onset of such diseases or conditions (e.g., Alzheimer's disease), or to treat a subject in the early stages of such diseases or conditions, or that is developing such a disease or condition, in order to prevent or inhibit development of the condition or disease.

An inhibitory peptide or pharmaceutical composition of the invention is sometimes referred to herein as an "inhibitor." An "effective amount" of an inhibitor of the invention is an amount that can elicit a measurable amount of a desired outcome, e.g. inhibition of Tau aggregation or cytotoxicity; for a diagnostic assay, an amount that can detect a target of interest, such as an Tau aggregate; or in a method of treatment, an amount that can reduce or ameliorate, by a measurable amount, a symptom of the disease or condition that is being treated.

A "subject" can be any subject (patient) having aggregated (fibrillated) Tau molecules associated with a condition or disease which can be treated by a method of the present invention. In one embodiment of the invention, the subject has Alzheimer's disease. Typical subjects include vertebrates, such as mammals, including laboratory animals, dogs, cats, non-human primates and humans.

The inhibitors of the invention can be formulated as pharmaceutical compositions in a variety of forms adapted to the chosen route of administration, for example, orally, nasally, intraperitoneally, or parenterally, by intravenous, intramuscular, topical or subcutaneous routes, or by injection into tissue.

Suitable oral forms for administering the inhibitors include lozenges, troches, tablets, capsules, effervescent tablets, orally disintegrating tablets, floating tablets designed to increase gastric retention times, buccal patches, and sublingual tablets.

The inhibitors of the invention can be systemically administered, e.g., orally, in combination with a pharmaceutically acceptable vehicle such as an inert diluent or an assimilable edible carrier, or by inhalation or insufflation. They can be enclosed in coated or uncoated hard or soft shell gelatin capsules, can be compressed into tablets, or can be incorporated directly with the food of the patient's diet. For oral therapeutic administration, the compounds can be combined with one or more excipients and used in the form of ingestible tablets, buccal tablets, troches, capsules, elixirs, suspensions, syrups, wafers, and the like. For compositions suitable for administration to humans, the term "excipient" is meant to include, but is not limited to, those ingredients described in Remington: The Science and Practice of Pharmacy, Lippincott Williams & Wilkins, 21st ed. (2006) (hereinafter Remington's).

The inhibitors can be combined with a fine inert powdered carrier and inhaled by the subject or insufflated. Such compositions and preparations should contain at least 0.1% compounds. The percentage of the compositions and preparations may, of course, be varied and may conveniently be between about 2% to about 60% of the weight of a given unit dosage form.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it may contain, in addition to materials of the above type, a liquid carrier, such as a vegetable oil or a polyethylene glycol. A syrup or elixir may contain the active compound, sucrose or fructose as a sweetening agent, methyl and propylparabens as preservatives, a dye and flavoring such as cherry or orange flavor.

Various other materials can be present as coatings or to otherwise modify the physical form of the solid unit dosage form. For instance, tablets, pills, or capsules can be coated with gelatin, wax, shellac or sugar and the like. Of course, any material used in preparing any unit dosage form should be pharmaceutically acceptable and substantially non-toxic in the amounts employed.

In addition, the inhibitors can be incorporated into sustained-release preparations and devices. For example, the inhibitors can be incorporated into time release capsules, time release tablets, and time release pills. In some embodiments, the composition is administered using a dosage form selected from the group consisting of effervescent tablets, orally disintegrating tablets, floating tablets designed to increase gastric retention times, buccal patches, and sublingual tablets.

The inhibitors may also be administered intravenously or intraperitoneally by infusion or injection. Solutions of the inhibitors can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the compounds which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants.

Sterile injectable solutions are prepared by incorporating the compounds in the required amount in the appropriate solvent with various of the other ingredients enumerated above, as required, followed by filter sterilization. In the case of sterile powders for the preparation of sterile injectable solutions, the preferred methods of preparation are vacuum drying and freeze drying techniques, which yield a powder of the active ingredient plus any additional desired ingredient present in the previously sterile-filtered solutions.

Useful solid carriers include finely divided solids such as talc, clay, microcrystalline cellulose, silica, alumina and the like. Other solid carriers include conventional nontoxic polymeric nanoparticles or microparticles. Useful liquid carriers include water, alcohols or glycols or water/alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Useful dosages of the peptides or pharmaceutical compositions of the invention can be determined by comparing their in vitro activity, and in vivo activity in animal models. Methods for the extrapolation of effective dosages in mice, and other animals, to humans are known to the art. For example, the concentration of the compounds in a liquid composition, such as a lotion, can be from about 0.1-25% by weight, or from about 0.5-10% by weight. The concentration in a semi-solid or solid composition such as a gel or a powder can be about 0.1-5% by weight, or about 0.5-2.5% by weight.

Effective dosages and routes of administration of agents of the invention are conventional. The exact amount (effective dose) of the agent will vary from subject to subject, depending on, for example, the species, age, weight and general or clinical condition of the subject, the severity or mechanism of any disorder being treated, the particular agent or vehicle used, the method and scheduling of administration, and the like. A therapeutically effective dose can be determined empirically, by conventional procedures known to those of skill in the art. See, e.g., The Pharmacological Basis of Therapeutics, Goodman and Gilman, eds., Macmillan Publishing Co., New York. For example, an, effective dose can be estimated initially either in cell culture assays or in suitable animal models. The animal model may also be used to determine the appropriate concentration ranges and routes of administration. Such information can then be used to determine useful doses and routes for administration in humans. A therapeutic dose can also be selected by analogy to dosages for comparable therapeutic agents.

The particular mode of administration and the dosage regimen will be selected by the attending clinician, taking into account the particulars of the case (e.g., the subject, the disease, the disease state involved, and whether the treatment is prophylactic). Treatment may involve daily or multi-daily doses of compound(s) over a period of a few days to months, or even years.

In general, however, a suitable dose will be in the range of from about 0.001 to about 100 mg/kg, e.g., from about 0.01 to about 100 mg/kg of body weight per day, such as above about 0.1 mg per kilogram, or in a range of from about 1 to about 10 mg per kilogram body weight of the recipient per day. For example, a suitable dose can be about 1 mg/kg, 5 mg/kg, 10 mg/kg, 20 mg/kg, or 30 mg/kg of body weight per day.

The inhibitors are conveniently administered in unit dosage form; for example, containing 0.05 to 10000 mg, 0.5 to 10000 mg, 5 to 1000 mg, or about 100 mg of active ingredient per unit dosage form. In some embodiments, the dosage unit contains about 0.1 mg, about 0.5 mg, about 1 mg, about 10 mg, about 25 mg, about 50 mg, about 75 mg, or about 100 mg, of active ingredient.

Examples, Elements and Biological Aspects of the Invention

VQIINK Forms an Extensive Steric Zipper Interface

To understand the forces that drive aggregation of Tau and to enable the design of inhibitors of aggregation of Tau40, we crystallized a ten residue Tau segment with sequence KVQIINKKLD (SEQ ID NO: 1) and determined its 1.5 Å resolution structure by MicroED. Like VQIVYK (SEQ ID NO: 9), this VQIINK (SEQ ID NO: 11)-containing segment forms a face-to-face Type 1 homo-steric zipper. That is, the protofilament is formed from the tight mating of identical parallel β-sheets, which are anti-parallel to each other[15]. The VQIINK (SEQ ID NO: 11) zipper shows tighter side chain interdigitation than the VQIVYK (SEQ ID NO: 9) zipper (FIG. 1B), having a shape complementarity of 0.77 compared to 0.72 for VQIVYK (SEQ ID NO: 9). Additionally VQIINK (SEQ ID NO: 11) buries greater surface area, 168 Å$^2$ compared to 75 Å$^2$ for VQIVYK (SEQ ID NO: 9). These measures of the strength of interfaces provide evidence that the zipper interface of VQIINK (SEQ ID NO: 11) is stronger than the VQIVYK (SEQ ID NO: 9) interface.

Interface B

Figure 1B:
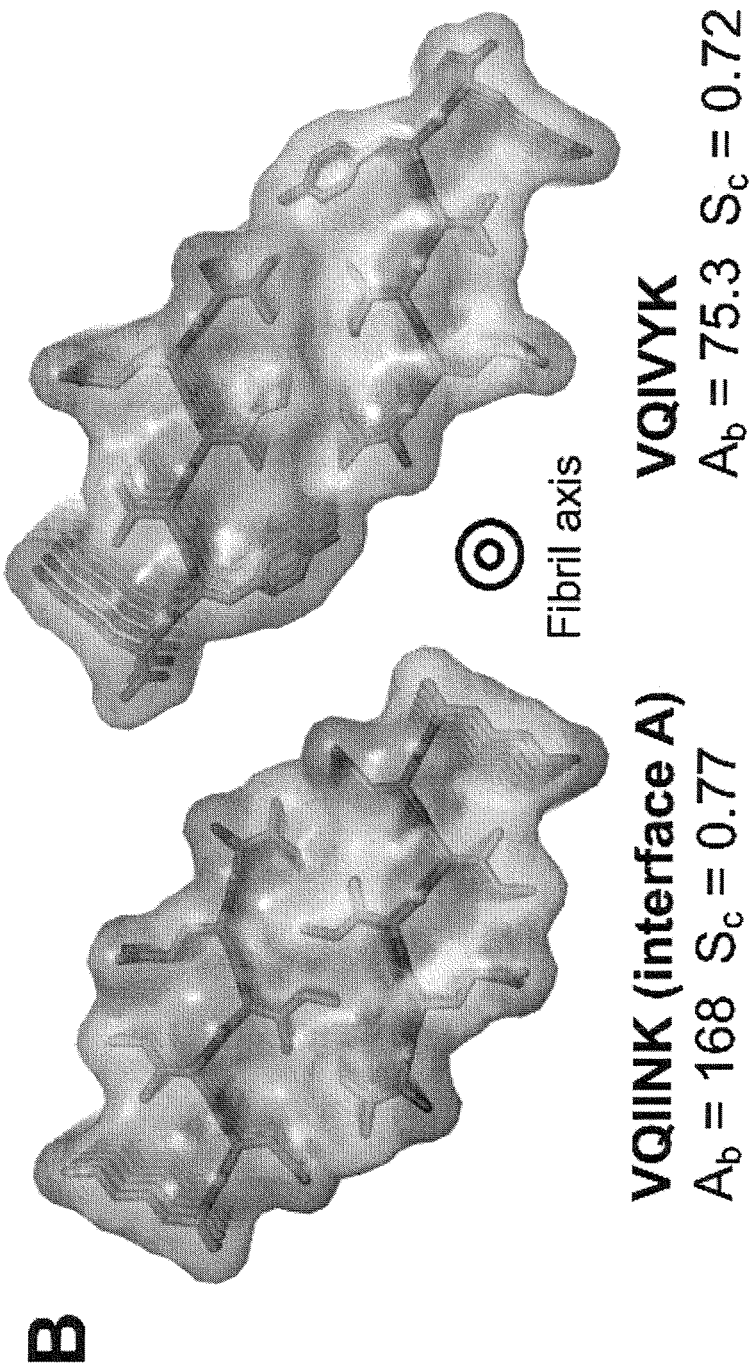
Figures 1C, 1D:
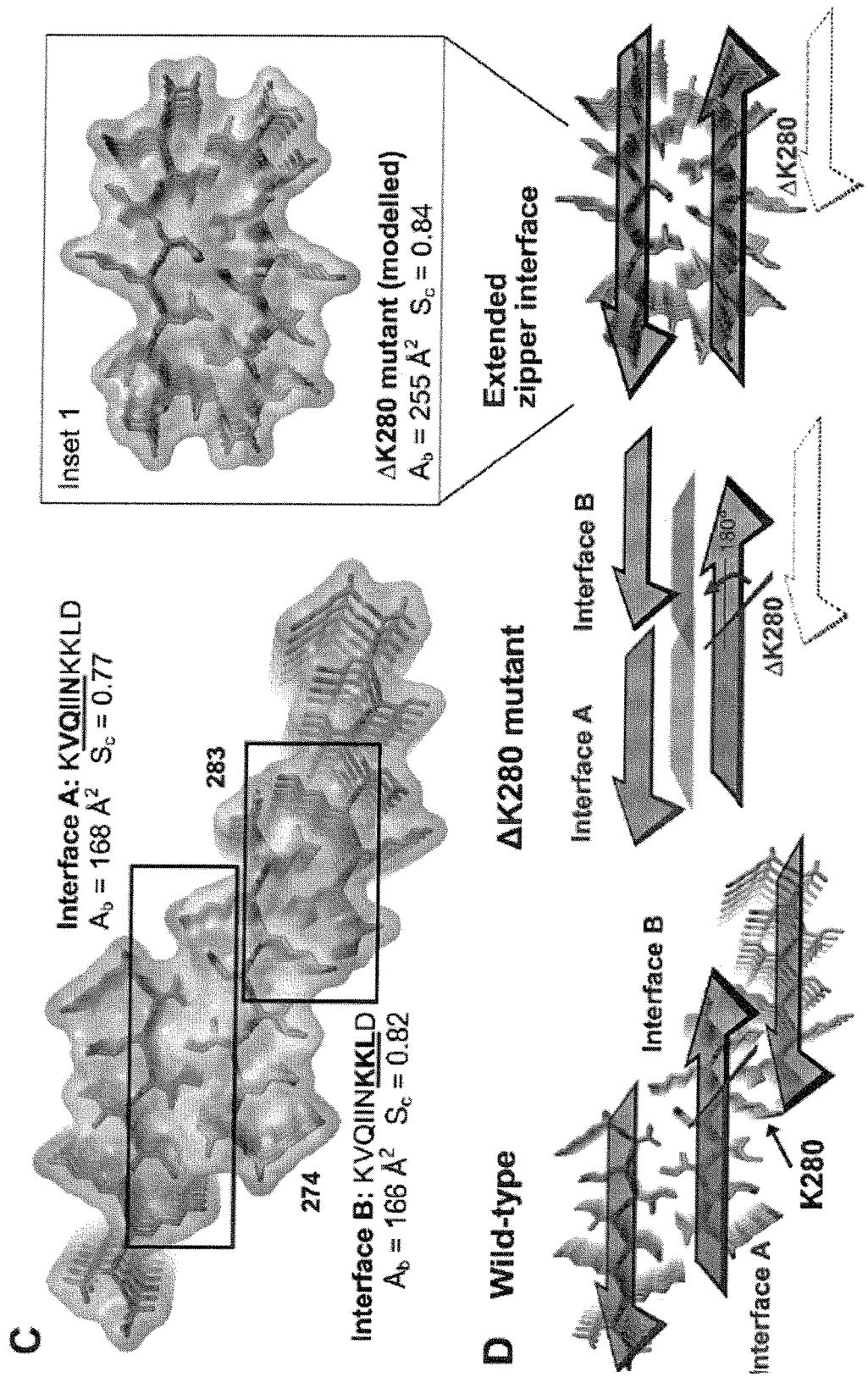

The ten residue VQIINK (SEQ ID NO: 11) segment revealed an unanticipated propensity to adopt a second steric zipper interface. The second zipper (referred to as Interface B) is formed by the C-terminal half of the segment, residues KKLD (SEQ ID NO: 24) (FIG. 1C). A sequence alignment comparing R2 and R3 shows that the equivalent residues in Repeat 3 are KVPD (SEQ ID NO: 25), which is not expected to adopt a comparable zipper since proline residues have a strong tendency to disrupt β-sheets and break amyloid structures'[6] (FIG. 1A). Furthermore an overlapping segment with the sequence LDLSN (SEQ ID NO: 26) in repeat 2, corresponding to amino acids 282-286, bears the features of an amphiphilic amyloidogenic sequence motif, whereas no additional sequences with these features are found in repeat 3.[17] This provides evidence that the potential to form a second extended steric zipper interface is limited to the Repeat 2 segment, VQIINK (SEQ ID NO: 11).

ΔK280 Mutant

In the wild-type segment structure, interfaces A and B are formed on opposite faces of the VQIINK (SEQ ID NO: 11) β-sheet. It is known that the ΔK280 mutation accelerates Tau fiber formation and has been linked to tauopathies.[1,18] Lys280 lies at the junction between interfaces A and B in our crystal structure (FIGS. 1C and D) and deleting K280 is expected to reverse the orientation of the C-terminal residues by 180° about the β-strand axis[19]. The result is to rotate the zipper-forming residues in interface B to the same face of the β-sheet as interface A, merging the two separate interfaces that lie on opposite faces in wild-type to a single extended zipper interface in the ΔK280 mutant (FIG. 1D, Inset 1). Modelling the steric zipper formed by the ΔK280 mutant shows that the extended interface formed by these predicted structural changes results in an extended zipper with high shape complementarity ($S_c$=0.84) and 50% more buried surface area ($A_b$=225 Å$^2$), explaining how the ΔK280 mutant could promote more rapid Tau aggregation and toxicity.

VQIINK Promotes Rapid Fiber Formation

Figure 2A:
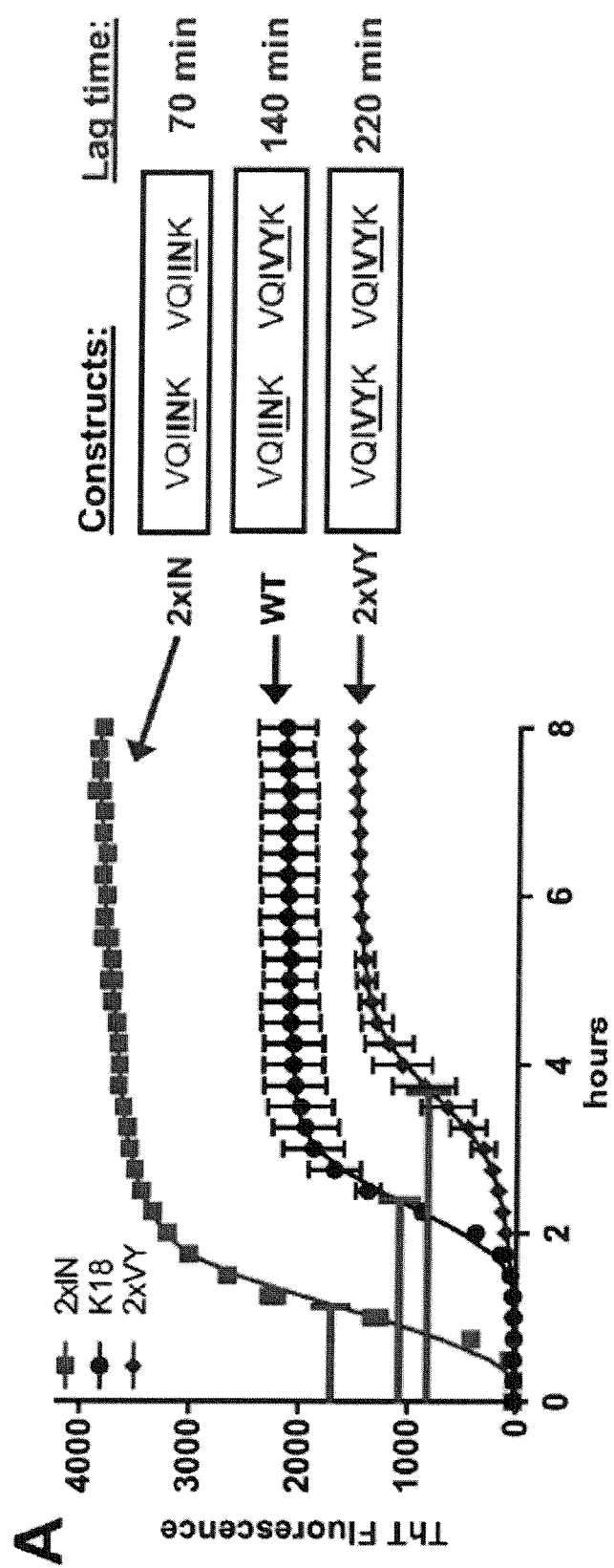
FIG. 2 Time dependence of fibrillization and oligomerization of the wild-type K18 construct and engineered 2×IN and 2×VY K18 constructs. (A) Averaged ThT fluorescence curves of engineered constructs (defined on the right) at 50 μM in the presence of heparin with shaking at 700 rpm 37° C. Lag times determined from the half-maximum values of the curves shown are given for the respective constructs in the diagram on the right. (B) Same as A except at a concentration of 10 μM without shaking. Error bars show the discrepancy of duplicate measurements. (C) Analysis of oligomers measured by S200 size exclusion chromatography.
Figures 2B, 2C:
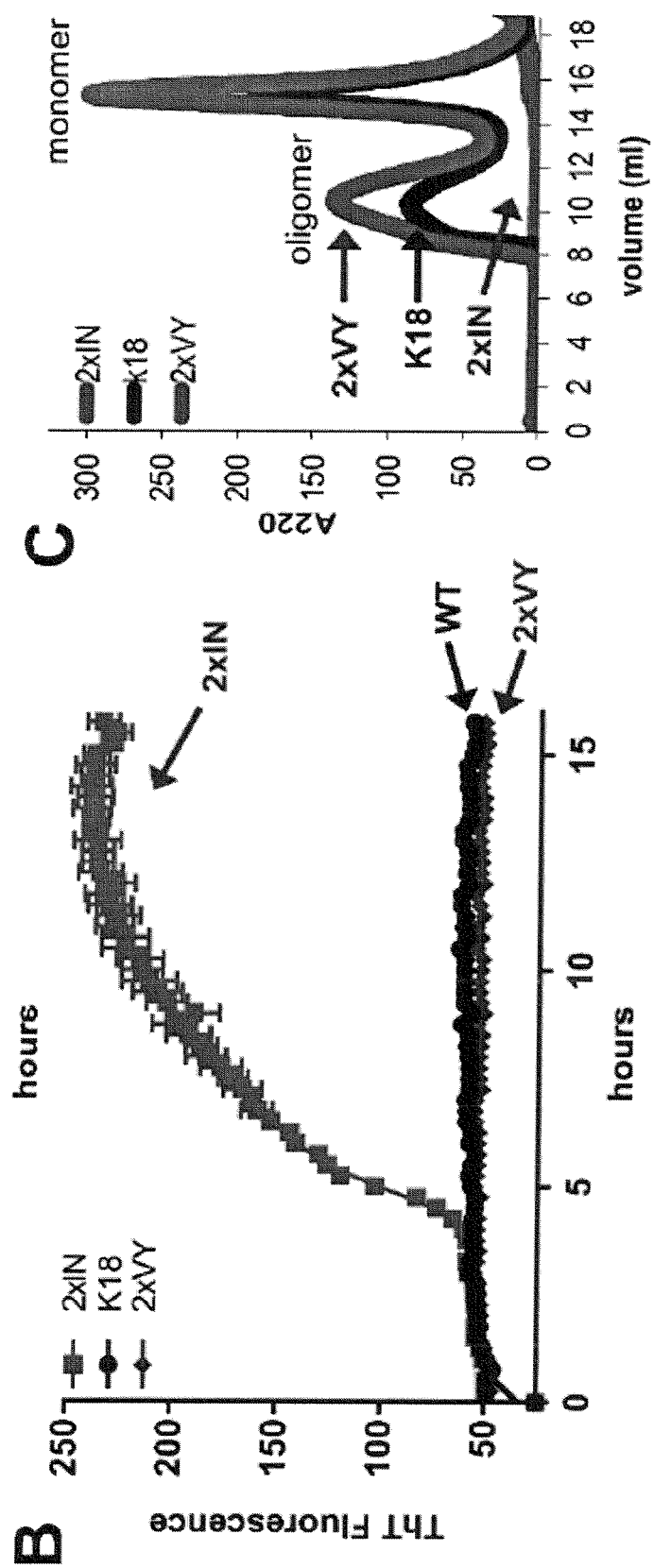

Given the observation that VQIINK (SEQ ID NO: 11) forms a more extensive steric zipper interface than VQIVYK (SEQ ID NO: 9), we wondered if VQIINK (SEQ ID NO: 11) would be a more potent driver of amyloid formation than VQIVYK (SEQ ID NO: 9). To test the possibility, we replaced the residues VY in VQIVYK (SEQ ID NO: 9) with IN, converting Tau K18 to an engineered form that contains two copies of VQIINK (SEQ ID NO: 11) (named 2×IN). Likewise 2×VY was constructed and compared with wild-type K18 to determine how the rates of fibril formation differ for constructs that contain only VQIINK (SEQ ID NO: 11) or VQIVYK (SEQ ID NO: 9) zipper segments. As shown by ThT fluorescence in FIG. 2A, 2×IN exhibits a greater rate of aggregation by shaking at 37° C. with heparin, forming fibrils in half the time of wild-type (70 min vs. 140 min to reach half maximum). 2×VY aggregates most slowly reaching half max after 220 min. The differences are accentuated at lower concentrations of Tau using gentler aggregation conditions, as shown in FIG. 2B where constructs are held quiescently at 37° C. with heparin. Even under these mild conditions, 2×IN readily aggregates while 2×VY and K18 show no detectable aggregation.

To evaluate how the VQIINK (SEQ ID NO: 11) and VQIVIYK (SEQ ID NO: 9) segments affect formation of soluble oligomers, Tau oligomers were fractionated by gel filtration chromatography. This approach has been used for K18 to separate monomer, oligomer, and fibrillar species.[20] Wild-type K18 forms a mixture of aggregates overnight, amyloid fibers and insoluble material are removed by ultracentrifugation and the resulting supernatant injected on a S200 size exclusion column separates into two peaks, one containing monomer and other oligomer (FIG. 2C, black). 2×VY produces a mixture of species similar to wild-type, whereas no remaining monomer or oligomer is detectable for 2×IN (FIG. 2C blue and green, respectively). Together, these data provide evidence that 2×IN rapidly fibrillizes in the presence of heparin, shifting the equilibrium away from monomeric and oligomeric species instead favoring rapid amyloid fiber formation.

Figure 3A:
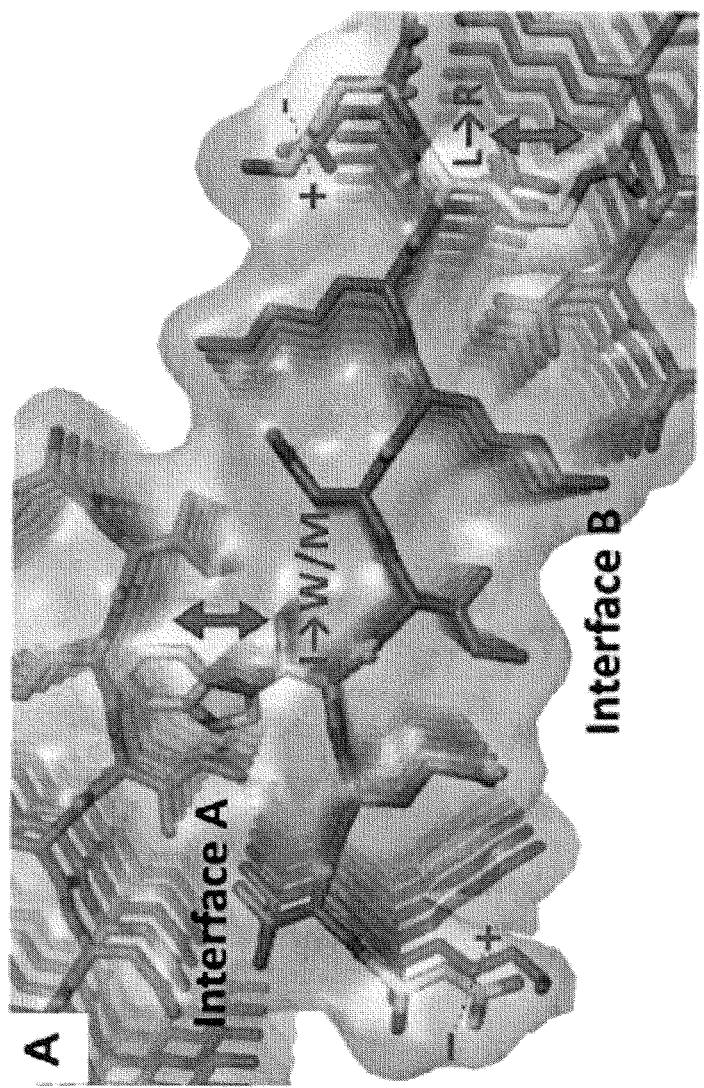
FIG. 3 Structure-based design of Phase 1 inhibitors of VQIINK (SEQ ID NO: 11) aggregation. (A) Logic of inhibitor design. The inhibitors (Table 2) bind on the tips of VQIINK (SEQ ID NO: 11) fibrils and introduce steric clashes that disrupt interfaces A and B. Based on the structures, the inhibitor sequences were designed as follows. Either a tryptophan (inhibitor WINK) or methionine (inhibitor MINK) were incorporated to block interface A. Both inhibitors contain an arginine to disrupt interface B. The ends of the inhibitor were charge reversed to promote electrostatic attraction of the inhibitor peptide to the fibril sequence. (B) The effects of designed inhibitors on the formation of fibrils of full Tau (Tau40) for 10 μM (left) or 25 μM (right) Tau40 plus a two-fold molar excess of WINK or MINK inhibitor peptide with shaking at 700 rpm at 37° C. (C) The effects of designed inhibitors on the transfer of fibrils of Tau40 into HEK293 biosensor stably expressing a full-length (4R1N P301S) YFP fusion. The cells were seeded with 125 nM Tau40 fiber (final concentration); the seeds were grown for 120 hours in the presence or absence of a two-fold excess of WINK or MINK. Representative cells containing aggregates are marked by red arrows, and cells without by white arrows. Percentages of cells with aggregates were calculated by dividing the number of aggregates in the field of view by the number of cells. Inset box shows a zoomed image from within the presented field of view. Both Panels B and C provide evidence that MINK is a more effective inhibitor than WINK.

The VQIINK (SEQ ID NO: 11) crystal structure was used as a template for structure-based inhibitor design (FIG. 3A). The native ten residue sequence that we crystallized was used as a starting point, and bulky amino acids were modelled into the zipper to identify residues that would best disrupt the observed interfaces. As summarized in Table 1, an Ile at position 4 and Leu at position 9 (corresponding to residues 1277 and L282 in the Tau40 protein sequence) were identified as key residues in interfaces A and B. Modelling indicated that interface A would be best disrupted by replacing the Ile at position 4 with either a Met or Trp, while interface B appeared to be best disrupted by Arg. Since the native peptide sequence targeted by the inhibitor is dipolar, beginning with a Lys and ending with an Asp, the terminal residues of the inhibitor peptide were charge reversed to promote electrostatic attraction with the binding interface.

Figure 3B:
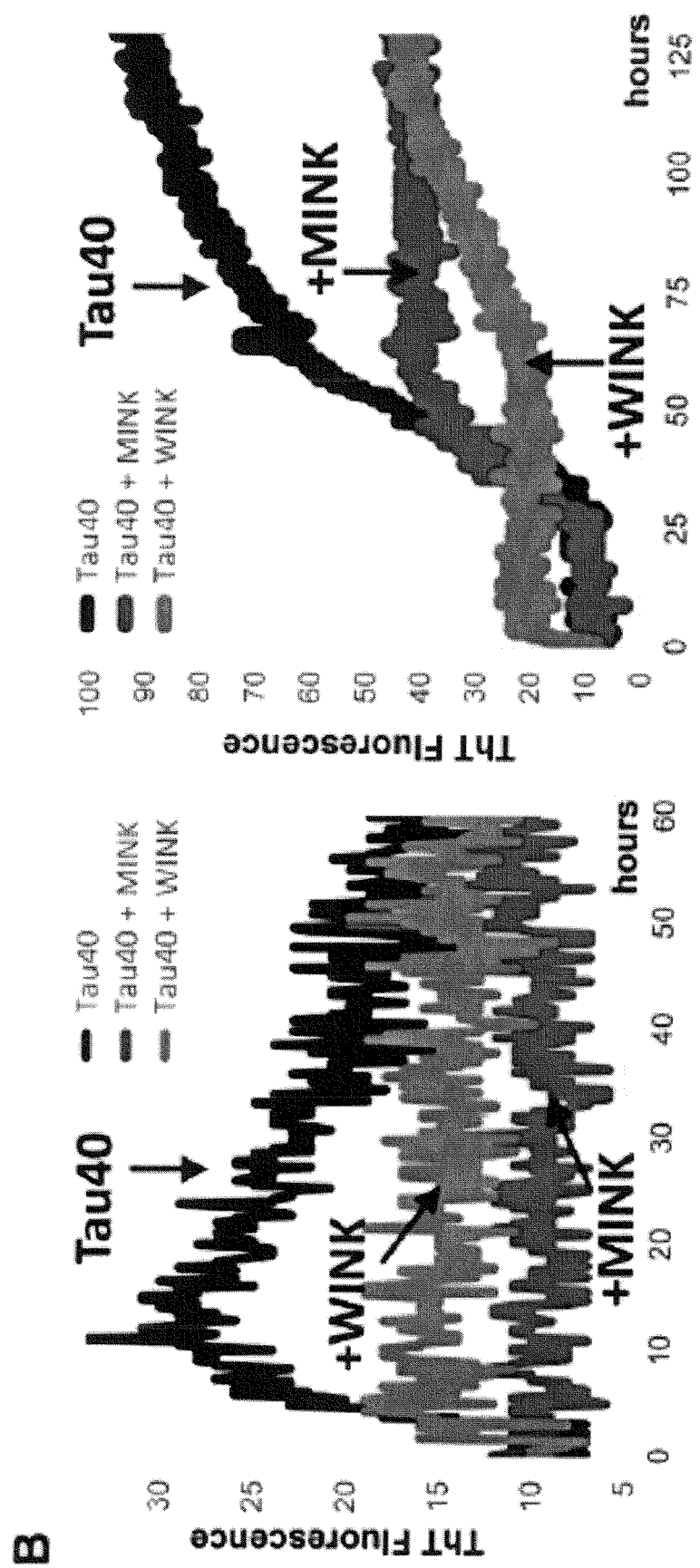

The effect on fibril formation of Tau40 of the two resulting VQIINK (SEQ ID NO: 11) inhibitors, MINK (which contains a Met at position 4 to disrupt interface A) and WINK (which instead contains a Trp) was evaluated in vitro using a ThT assay. At 10 μM Tau40, a two-fold mole excess of MINK outperformed WINK, with WINK reducing the amount of Tau40 aggregation to about half, and MINK completely inhibiting any detectable Tau40 fibril formation for at least 60 hours (FIG. 3B). At 25 μM Tau40 a two-fold mole excess of either MINK or WINK reduced Tau40 aggregation to about half.

TABLE 2

Amino acid sequences of Tau inhibitors, based on two structures of the VQIINK (SEQ ID NO: 11) interface.

| | Tau40 residue #s 274-283 | |
|---|---|---|
| | inhibitor position | 1-2-3-4-5-6-7-8-9-10 |
| Phase | Wild-type | K-V-Q-I-I-N-K-K-L-D (SEQ ID NO: 1) |
| Phase | MINK | D-V-Q-M-I-N-K-K-R-K (SEQ ID NO: 2) |
| | WINK | D-V-Q-W-I-N-K-K-R-K (SEQ ID NO: 3) |
| | RINK | D-V-Q-R-I-N-K-K-R-K (SEQ ID NO: 4) |
| | W-MINK | D-V-W-M-I-N-K-K-R-K (SEQ ID NO: 5) |
| | W-WINK | D-V-W-W-I-N-K-K-R-K (SEQ ID NO: 6) |
| | W-M-W-NK | D-V-W-M-W-N-K-K-R-K (SEQ ID NO: 7) |
| | W-W-W-NK | D-V-W-W-W-N-K-K-R-K (SEQ ID NO: 8) |

The top row lists the residue number from the native Tau40 sequence. The second row lists the residue position number in the inhibitor peptide. Row 3 is the native sequence from the wild-type human Tau40, and rows 4-10 are inhibitor peptide sequences tested in this paper. Residues at positions 4 and 9 are critical for forming Interfaces A and B, respectively. Residues 3 and 5 comprise Interface C.

Figure 3C:
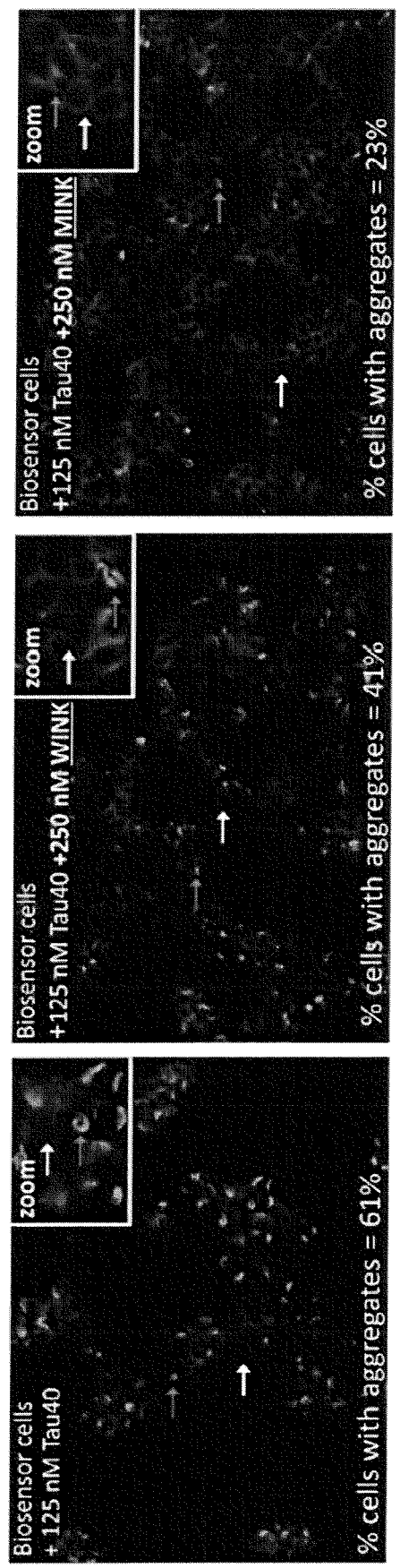

Recent evidence suggests that aggregated Tau can spread from cell to cell in a prion-like manner, apparently by seeding Tau in the recipient cell into fibrils.[21] To test whether the VQIINK (SEQ ID NO: 11) inhibitors are capable of blocking the spread of Tau fibers by seeding, Tau40 monomer was incubated at 37° C. shaking with heparin in the presence or absence of MINK or WINK before seeding HEK293 biosensor cells stably expressing full-length Tau 4R1N P301S-EYFP, similar to previous experiments that used biosensor cells to assay seeding by exogenous Tau fibrils.[22] As shown in FIG. 3C, about 61% of the cells that were seeded with 125 nM unlabeled Tau40 fiber in the absence of inhibitor produced intracellular aggregates. Cells seeded with Tau40 fiber grown with MINK or WINK reduced the percentage of seeded cells to 23 and 41%, respectively. Qualitatively these VQIINK (SEQ ID NO: 11) inhibitors improved the appearance of cells resulting in more typical monolayer growth rather than rounded morphology (FIG. 3C).

Figure 4A:
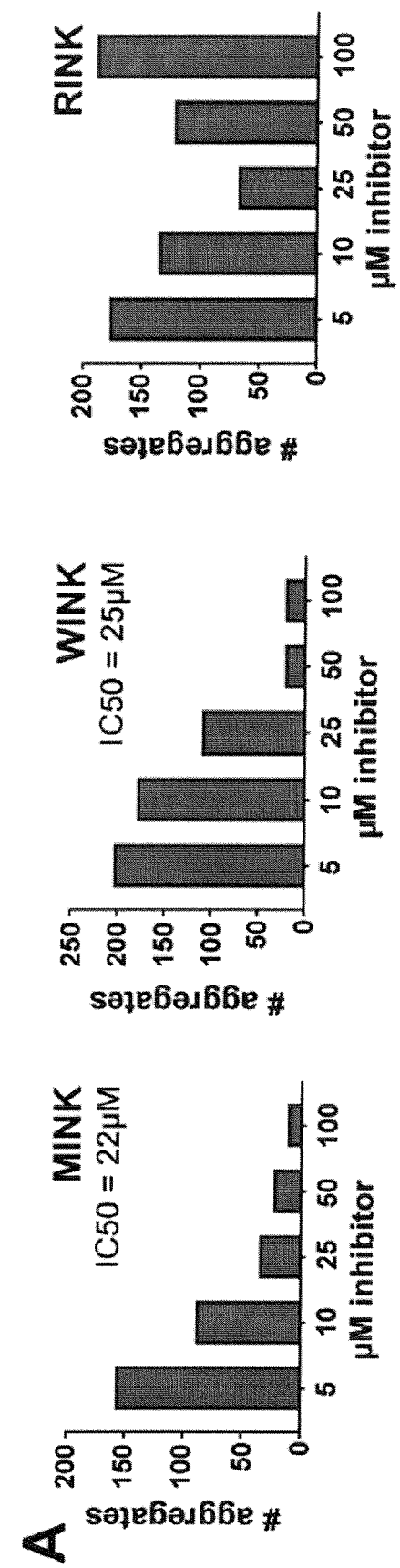
FIG. 4 The inhibition of Tau aggregation by Phase 2 designed inhibitors. (A) Full-length Tau-YFP biosensor cells seeded with pre-formed Tau40 fibers treated with MINK, WINK, or RINK inhibitor at indicated concentrations. (B and C) Comparison of the 10-residue and 6-residue VQIINK (SEQ ID NO: 11) MicroED structures, viewed down the fibril axes. (B) The 10-residue segment forms a face-to-face Class 1 zipper, whereas (C) the 6-residue VQIINK (SEQ ID NO: 11) segment forms a face-to-back Class 4 zipper[9]. (D) As in A except using Phase 2 VQIINK (SEQ ID NO: 11) inhibitors (described in text) that block interfaces A, B and C. (E) Fluorescence images of seeded cells treated with 5 or 25 μM W-MINK inhibitor. Representative cells containing aggregates are marked by red arrows, and cells without by white arrows.

To test whether VQIINK (SEQ ID NO: 11) inhibitors can cap pre-formed fibers to block their spread, Tau40 amyloid fibrils were incubated with varying concentrations of inhibitor before applying to biosensor cells and measuring seeding. In addition, a third VQIINK (SEQ ID NO: 11) inhibitor, RINK which contains an Arg at position 4, was also tested. As shown in FIG. 4A, MINK and WINK inhibit seeding by Tau40 fibers in a concentration dependent fashion. From the dose-response curves shown, IC50 values of 22 and 25 µM were calculated for MINK and WINK. The RINK inhibitor, however inhibited more poorly than MINK and WINK suggesting that Met and Trp are better suited than Arg for incorporating into the fiber backbone and disrupting zipper formation at interface A.

Design of Phase 2 Inhibitors Based on a Second Polymorph

Figures 4B, 4C:
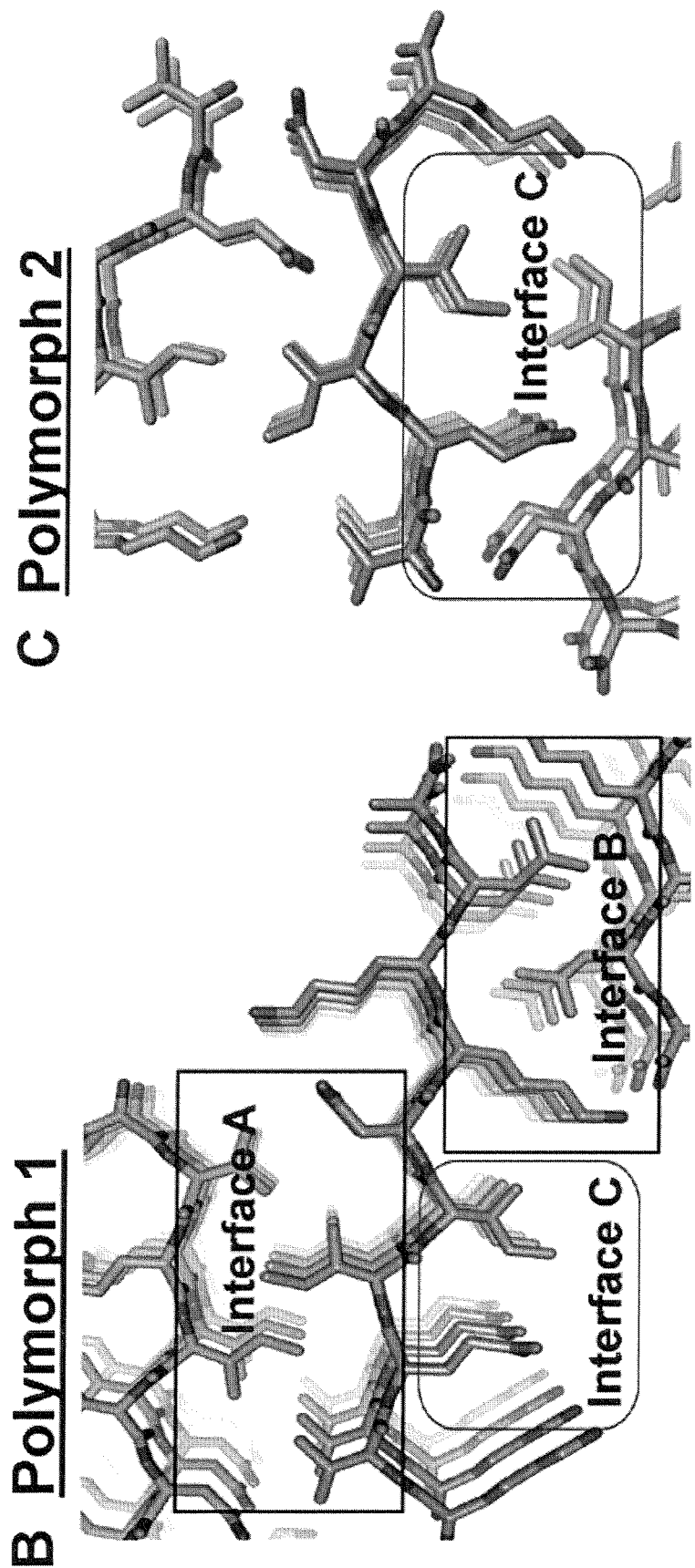

We sought and discovered a second structural polymorph of amyloid fibrils formed by the VQIINK (SEQ ID NO: 11) segment. Our rationale was the report that distinct strains of HEK biosensor cells are apparently caused by seeding with distinct aggregated forms of Tau[22], and that K18 which contains VQIINK (SEQ ID NO: 11) in addition to VQIVYK (SEQ ID NO: 9) exhibits conformational heterogeneity whereas K19, which contains only VQIYVK (SEQ ID NO: 9) does not[23]. We screened for and found nanocrystals of the VQIINK (SEQ ID NO: 11) segment and were able to determine their atomic structure by MicroED. This crystal reveals a Class 4, face-to-back steric zipper, driven by Gln and Ile sidechains on the opposite face of the VQIINK (SEQ ID NO: 11) β-strand. We term this Interface C (FIG. 4C). Interface C buries approximately the same surface area as Interface A. Apparently the VQIINK (SEQ ID NO: 11) segment of Tau is capable of forming at least three distinct steric zipper interactions, leading to at least three distinct amyloid fibrils and potentially three distinct phenotypic downstream effects.

We hypothesize that the interfaces observed in our two crystal structures represent the actual surfaces used by Tau40 to form different aggregate subpopulations. To test this, we re-engineered MINK and WINK to incorporate a third steric clash that would disrupt Interface C, in addition to Interfaces A and B. We reasoned that if multiple subpopulations of aggregates can simultaneously exist as a mixture in solution, or perhaps in a mixture of cells, then one inhibitor capable of targeting Interfaces A, B, and C should be more potent than the MINK and WINK inhibitors alone, which target only interfaces A and B.

Figure 4D:
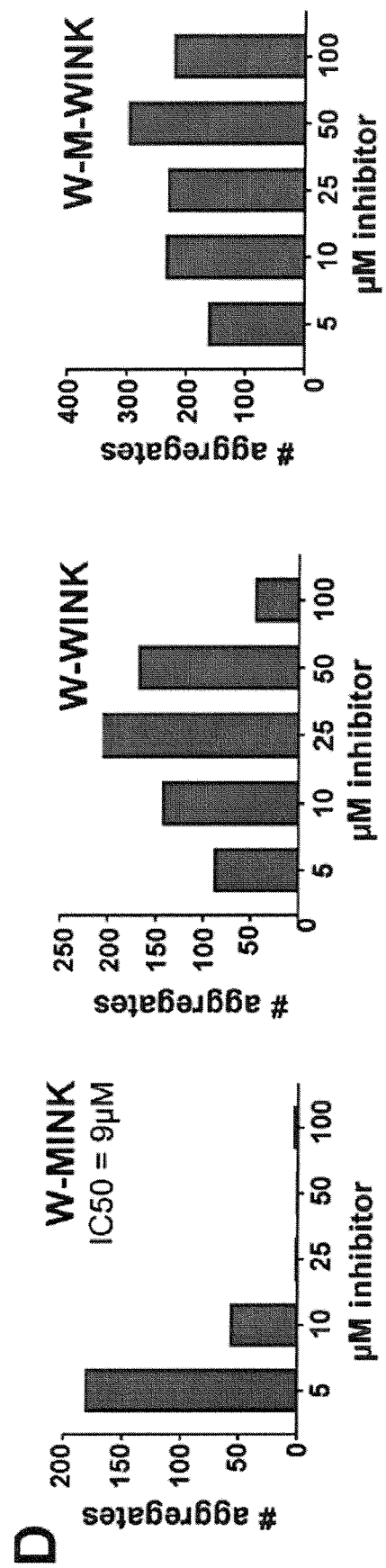

This hypothesis led to our Phase 2 inhibitors (Table 2, FIG. 4D). As shown in FIG. 4C, a Gln and Ile at positions 3 and 5 form the basis of Interface C. Modelling indicated that substituting these positions with a tryptophan would be most destabilizing to the steric zipper structure. As summarized in Table 2, the resulting iterations of MINK and WINK incorporate a Trp steric clash at position 3 (referred to as W-MINK and W-WINK), or positions 3 and 5.

Figure 4E:
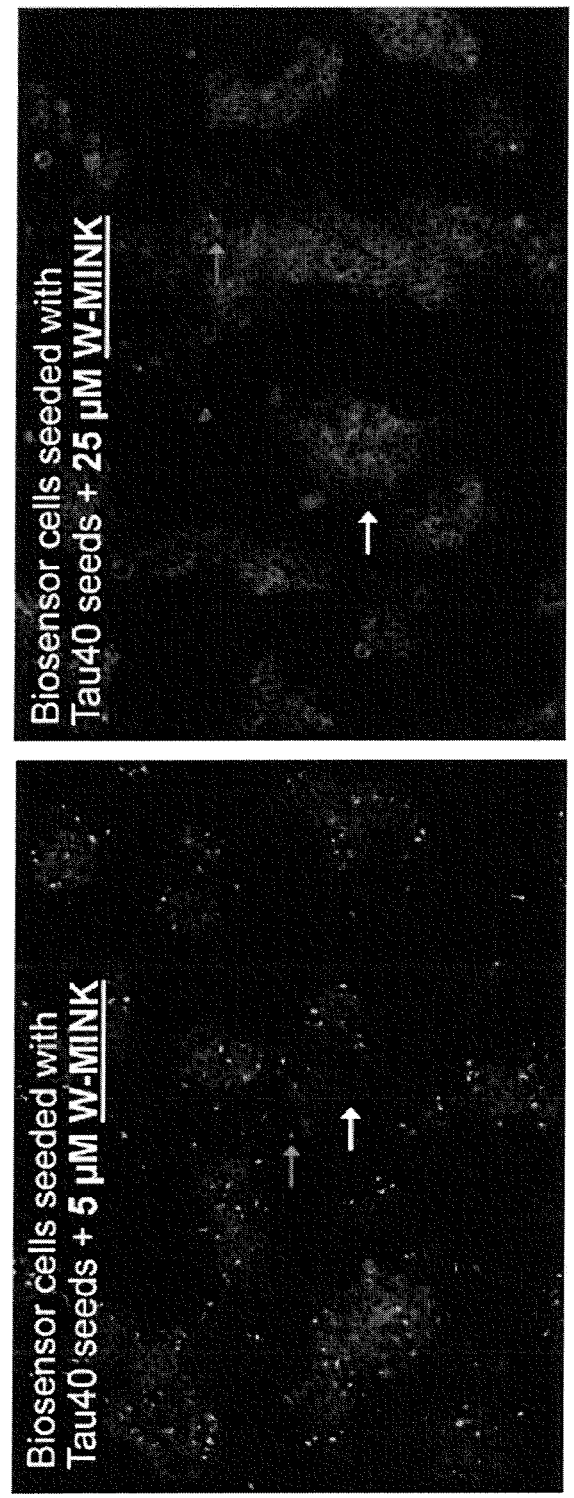

As shown in FIG. 4D the Phase 2 inhibitor W-MINK blocked Tau40 seeding more effectively than MINK, having an IC50 of 9 µM compared to 22 µM for MINK. Fluorescence images of seeded cells at two selected W-MINK concentrations, 5 and 25 µM shown in FIG. 4E illustrate the effect W-MINK has on seeding by Tau40 fibers. At 5 µM W-MINK, Tau40 fibers are still able to induce seeding in biosensor cells whereas at 25 µM W-MINK, seeding by Tau40 fibers is no longer observed. By contrast the W-WINK inhibitor performed more poorly than W-MINK, possibly owing to a destabilizing effect that two tryptophans in series may have on incorporating into the amyloid chain. Similarly, we found that substitution of the second Ile at position 5 in Interface C with Trp failed to inhibit Tau40 seeding, regardless of whether position 4 is Met or Trp.

Prior to the two atomic structures of the VQIINK (SEQ ID NO: 11) segment reported here, understanding of the atomic basis for amyloid aggregation of Tau was limited. The crystals of Tau segments that included the VQIINK (SEQ ID NO: 11) segment were invariably some ten thousand times smaller in volume than crystals of the other fibril-driving segment VQIVYK (SEQ ID NO: 9), and thus too tiny for manipulation and X-ray data collection. Electron diffraction came to the rescue, providing atomic resolution structures of fibrils of both the 10-residue amyloid forming segment with sequence KVQIINKKLD (SEQ ID NO: 1) and the 6-residue structure of VQIINK (SEQ ID NO: 11) itself.

Both structures reveal a propensity of VQIINK (SEQ ID NO: 11) to form tightly interdigitated steric-zipper interfaces that appear to be more adhesive than the interface of VQIVYK (SEQ ID NO: 9). Biochemical studies support this interpretation showing that engineered Tau constructs containing only VQIINK (SEQ ID NO: 11) aggregate more rapidly than wild-type and constructs containing only VQIVYK (SEQ ID NO: 9) instead accrue a mixture of monomer, oligomer and fiber. These data indicate that VQIINK (SEQ ID NO: 11) is a potent driver of Tau amyloid aggregation, and that it is likely an excellent target for inhibitors of Tau fibril formation. Our data also provides evidence that VQIVYK (SEQ ID NO: 9) favors production of Tau oligomers, potentially owing to its slower aggregation into fibrils.

Our VQIINK (SEQ ID NO: 11) structures explain observations that have been made previously. The structure of the ten residue segment shows that Ile277 projects into Interface A, forming the centerpiece for the aggregation of this motif. Previous studies highlighted the importance of Ile277 by showing that I277P disrupts Tau amyloid fiber structure.[18] Additionally as described in FIG. 1D, our structure provides insight into how deletion of Lys280, can enhance Tau fibril formation.

These two VQIINK (SEQ ID NO: 11)-containing structures enabled the design of VQIINK inhibitors that act on full-length Tau by capping the ends of Tau fibrils to prevent template-assisted filament growth[10,24]. The VQIINK (SEQ ID NO: 11) inhibitors tested here slow full-length Tau aggregation in vitro and furthermore, for the first time, block seeding induced by Tau40 fibers in HEK293 biosensor cells. We anticipate that combining structure-based VQIINK (SEQ ID NO: 11) and VQIVYK (SEQ ID NO: 9) inhibitors will allow for the discovery of synergistic pairs of inhibitors that are more potent than individual capping inhibitors alone.

The effectiveness of inhibition depends on the stage of administration of the inhibitor. That is, the concentration of inhibitor required to block seeding by pre-formed fibers is about 100 times greater than the amount required when inhibitor is added to monomeric Tau prior to initiating aggregation by shaking and the addition of heparin, when 250 nM inhibitor effectively inhibited seeding. The greater amount of inhibitor required to block pre-formed fibers likely stems from the propensity of mature fibers to extend unabated, producing longer fibers with more surface area for seeding by secondary nucleation and/or fragmentation into smaller species that produce new sites for primary nucleation. This observation may highlight the importance of early disease intervention with amyloid inhibitors, underscoring the need for sensitive disease biomarkers.

Our structures of VQIINK (SEQ ID NO: 11) also provide evidence that a structural basis for the mysterious phenomenon of Tau strains.[22,25] Whereas strains in microorganisms are different phenotypes encoded by different nucleic acid sequences, strains in amyloid diseases are different phenotypes encoded by different fibril structures. Different fibril structures, in turn, are likely encoded by formation of different steric zippers.[26] Three distinctly different steric zippers emerged from our two VQIINK (SEQ ID NO: 11) structures: interfaces A, B and C. The existence of these distinct interfaces may begin to explain how different Tau strains originate at the molecular level.

We speculate that each distinct tauopathy may be associated with a given Tau strain[22,25], or in other words, could be associated with a given fibril structure. If so, inhibitors designed to disrupt a given steric zipper could probe, or potentially inhibit, a given tauopathy. Some support for this speculation comes from our studies of fibril inhibition. Incorporating information about each of the A, B, C interfaces into a single inhibitor improved the overall potency (reducing the IC50), suggesting that each of the interfaces contributes to aggregation of full-length Tau in solution. Knowing the structures of these polymorphs thus provides an opportunity for future studies in which Tau strains originating from different tauopathies are probed with an inhibitor to each interface. That is, selective inhibitors of the A, B, or C interface may identify strain sensitivities. Similarly, these inhibitors may be tools to understand which molecular interfaces contribute to formation of soluble oligomers.

Illustrative Methods and Materials of the Invention
Crystallization, Data Collection, and Structure Solution Nanocrystals of KVQIINKKLD (SEQ ID NO: 1) synthetic peptide (purchased from Genscript) were prepared from 30 mg/ml stocks dissolved in water by the addition of 45 mM arachidonic acid to concentrated peptide. Subsequently crystals were grown in batch at 37° C. by the addition of 10 μl of precipitant (32% PEG10K in 100 mM phosphate citrate, pH 4.2) to 5 μl of protein. After 18 hours nanocrystals were resuspended by pipetting, spun down in an epitube and the resulting crystalline pellet was washed three times with water. Nanocrystals of VQIINK (SEQ ID NO: 11) peptide (purchased from Genscript) were grown by vapor diffusion from peptide at 15 mg/ml as a 1:2 drop ratio (protein:reservoir) from 0.29 M LiNO3, 24% (w/v) PEG 3350 at 18° C. and similarly harvested for data collection.

MicroED data were collected by spotting 2-3 μl of crystals onto TEM grids with carbon film support and plunge frozen in liquid ethane using a Vitrobot Mark IV (FEI). Diffraction images were collected on an FEI Tecnai F20 TEM at 200 kV as a continuous rotation tilt series at a rate of 0.2° per second with 2 second exposures per image. Diffraction data from several crystals were indexed, merged and scaled with XDS and XSCALE.[27] Molecular replacement was performed with Phaser[28] using a polyalanine search model composed of an ideal β-strand. The structure of VQIINK (SEQ ID NO: 11) was solved using a truncated version of KVQIINKKLD (SEQ ID NO: 1) comprising residues 2-7 (VQIINK (SEQ ID NO: 11)) as a search model in Phaser. Crystallographic refinements were performed using the programs Refmac[29], Buster[30], and Coot[31].

Protein Expression and Purification

Human Tau wild-type K18 (residues 244-372), 2×IN (V308I/Y309N) and 2×VY (I278V/N279Y) were expressed in a pNG2 vector[32] in BL21-Gold E. coli cells grown in LB to an OD600=0.8. Cells were induced with 0.5 mM IPTG for 3 hours at 37° C. and lysed by sonication in 20 mM MES buffer (pH 6.8) with 1 mM EDTA, 1 mM MgCl$_2$, 1 mM DTT and HALT protease inhibitor before addition of NaCl 500 mM final concentration. Lysate was boiled for 20 minutes and the clarified by centrifugation at 15,000 rpm for 15 minutes and dialyzed to 20 mM MES buffer (pH 6.8) with 50 mM NaCl and 5 mM DTT. Dialyzed lysate was purified on a 5 ml HighTrap SP ion exchange column and eluted over a gradient of NaCl from 50 to 550 mM. Proteins were polished on a HiLoad 16/600 Superdex 75 μg in 10 mM Tris (pH 7.6) with 100 mM NaCl and 1 mM DTT, and concentrated to ~20-60 mg/ml by ultrafiltration using a 3 kDa cutoff.

Human Tau40 (residues 1-441) was expressed in pET28b with a C-terminal His-tag in BL21-Gold E. coli cells grown in TB to an OD600=0.8. Cells were induced with 0.5 mM IPTG for 3 hours at 37° C. and lysed by sonication in 50 mM Tris (pH 8.0) with 500 mM NaCl, 20 mM imidazole, 1 mM beta-mercaptoethanol, and HALT protease inhibitor. Cells were lysed by sonication, clarified by centrifugation at 15,000 rpm for 15 minutes, and passed over a 5 ml HisTrap affinity column. The column was washed with lysis buffer and eluted over a gradient of imidazole from 20 to 300 mM. Fractions containing purified Tau40 were dialyzed into 50 mM MES buffer (pH 6.0) with 50 mM NaCl and 1 mM beta-mercaptoethanol and purified by cation exchange as described for K18. Peak fractions were polished on a HiLoad 16/600 Superdex 200 μg in 1×PBS (pH 7.4), and concentrated to ~20-60 mg/ml by ultrafiltration using a 10 kDa cutoff.

Inhibitor Peptides

All of the inhibitor peptides shown in Table 2 were synthesized by Genscript with minimum purities of 90% and dissolved in deionized water to a final stock concentration of 6 mM.

ThT Assay

Concentrated Tau protein was diluted into PBS buffer (pH 7.4) to a final concentration as indicated in the text. Proteins were shaken as solutions containing 75 μM ThT, 0.5 mg/ml heparin, 1 mM DTT, and a two-fold molar excess of inhibitor (when indicated) in 96-well plates with a plastic bead to enhance agitation. ThT fluorescence was measured with excitation and emission wavelengths of 440 and 480 nm, and averaged curves were generated from duplicate measurements.

Biosensor Cell Seeding

Engineered HEK293 cell lines stably expressing Tau40-YFP P301S, referred to as "tau biosensor cells" were engineered by Marc Diamond's lab at UTSW. Cells were maintained in DMEM (Life Technologies, cat. 11965092) supplemented with 10% (vol/vol) FBS (Life Technologies, cat. A3160401), 1% penicillin/streptomycin (Life Technologies, cat. 15140122), and 1% Glutamax (Life Technologies, cat. 35050061) at 37° C., 5% CO$_2$ in a humidified incubator. Tau40 aggregates were prepared in PBS (pH 7.4) with 1 mM DTT by shaking 25 μM Tau40 with 0.5 mg/ml heparin in the presence or absence inhibitor peptide, as indicated. Fibers were sonicated in a cuphorn water bath for 3 minutes before seeding cells. For seeding, fibers were diluted in OptiMEM (Life Technologies, cat. 31985070) and transfected using Lipofectamine 2000 (Life Technologies, cat. 11668027) according to the manufacturer's instructions. After seeding, cells were imaged using a ZEISS Axio Observer D1 fluorescence microscope using the YFP fluorescence channel and Tau aggregates were counted in ImageJ software. Dose-response curves were constructed for inhibitor peptides exhibiting concentration dependence and fit by nonlinear regression in Graphpad Prism.

| Data collection and atomic refinement statistics. | | |
|---|---|---|
| Structure | KVQIINKKLD (SEQ ID NO: 1) | VQIINK (SEQ ID NO: 11) |
| Data collection | | |
| Number of merged datasets | 12 | 3 |
| Space group | P2$_1$ | P2$_1$2$_1$2 |
| Cell dimensions | | |
| a, b, c (Å) | 27.1, 4.8, 32.4 | 20.4, 43.2, 4.8 |
| α, β, γ (°) | 90.0, 100.5, 90.0 | 90.0, 90.0, 90.0 |
| Resolution (Å) | 18.8-1.5 (1.68-1.50) * | 10.2-1.25 (1.40-1.25) * |
| R$_{merge}$ (%) | 25.0 | 23.9 |
| I/σ(I) | 5.2 (2.8) | 3.58 (1.59) |
| Completeness (%) | 84.8 (82.3) | 86.8 (71.6) |
| Redundancy | 9.1 | 4.4 |
| Refinement | | |
| Resolution (Å) | 18.8-1.5 | 10.18-1.25 |
| No. reflections | 2,203 | 1,226 |
| R$_{work}$/R$_{free}$ | 19.0/21.2 | 21.9/26.6 |
| No. atoms | | |
| Protein | 197 | 107 |
| Ligand/ion | 0 | 0 |
| Water | 2 | 0 |
| Overall B-factors (Å$^2$) | 16.9 | 15.3 |
| R.m.s. deviations | | |
| Bond lengths (Å) | 0.01 | 0.01 |
| Bond angles (°) | 1.5 | 1.4 |

* Values in parentheses refer to outermost shell of data

Tau 40 Polypeptide Sequence

```
NCBI Reference Sequence: NP_005901.2
                                              (SEQ ID NO: 10)
MAEPRQEFEVMEDHAGTYGLGDRKDQGGYTMHQDQEGDTDAGLKESPLQTP

TEDGSEEPGSETSDAKSTPTAEDVTAPLVDEGAPGKQAAAQPHTEIPEGTT

AEEAGIGDTPSLEDEAAGHVTQARMVSKSKDGTGSDDKKAKGADGKTKIAT

PRGAAPPGQKGQANATRIPAKTPPAPKTPPSSGEPPKSGDRSGYSSPGSPG

TPGSRSRTPSLPTPPTREPKKVAVVRTPPKSPSSAKSRLQTAPVPMPDLKN

VKSKIGSTENLKHQPGGGKVQIINKKLDLSNVQSKCGSKDNIKHVPGGGSV

QIVYKPVDLSKVTSKCGSLGNIHHKPGGGQVEVKSEKLDFKDRVQSKIGSL

DNITHVPGGGNKKIETHKLTFRENAKAKTDHGAEIVYKSPVVSGDTSPRHL

SNVSSTGSIDMVDSPQLATLADEVSASLAKQG
```

REFERENCES

1 Margittai, M. & Langen, R. Side Chain-dependent Stacking Modulates Tau Filament Structure. *Journal of Biological Chemistry* 281, 37820-37827, doi:10.1074/jbc.M605336200 (2006).
2 von Bergen, M. et al. Assembly of τ protein into Alzheimer paired helical filaments depends on a local sequence motif (306VQIVYK311) forming β structure. *Proceedings of the National Academy of Sciences* 97, 5129-5134, doi: 10.1073/pnas.97.10.5129 (2000).
3 Goedert, M., Eisenberg, D. S. & Crowther, R. A. *Annual Review of Neuroscience* 40, doi:DOI: 10.1146/annurev-neuro-072116-031153 (2017).
4 Schwarz, A. J. et al. Regional profiles of the candidate tau PET ligand recapitulate key features of Braak histopathological stages. *Brain* 139, 1539-1550, doi:10.1093/brain/aww023 (2016).
5 Manczak, M. & Reddy, P. H. Abnormal interaction of oligomeric amyloid-β with phosphorylated tau: implications to synaptic dysfunction and neuronal damage. *Journal of Alzheimer's disease: JAD* 36, 285-295, doi: 10.3233/JAD-130275 (2013).
6 Seward, M. E. et al. Amyloid-β signals through tau to drive ectopic neuronal cell cycle re-entry in Alzheimer's disease. *Journal of Cell Science* 126, 1278-1286, doi: 10.1242/jcs.1125880 (2013).
7 Brier, M. R. et al. Tau and AP imaging, CSF measures, and cognition in Alzheimer's disease. *Science Translational Medicine* 8, 338ra366-338ra366, doi:10.1126/scitranslmed.aaf2362 (2016).
8 von Bergen, M. et al. Mutations of tau protein in frontotemporal dementia promote aggregation of paired helical filaments by enhancing local beta-structure. *Journal of Biological Chemistry*, doi:10.1074/jbc.M105196200 (2001).
9 Sawaya, M. R. et al. Atomic structures of amyloid cross-[bgr] spines reveal varied steric zippers. *Nature* 447, 453-457, doi:http://www.nature.com/nature/journal/v447/n7143/suppinfo/nature05695_S1.thml (2007).
10 Sievers, S. A. et al. Structure-based design of non-natural amino-acid inhibitors of amyloid fibril formation. *Nature* 475, 96-100, doi:http://www.nature.com/nature/journal/v475/n7354/abs/nature10154-f1.2.html#supplementary-information (2011).
11 Zheng, J. et al. Macrocyclic β-Sheet Peptides That Inhibit the Aggregation of a Tau-Protein-Derived Hexapeptide. *Journal of the American Chemical Society* 133, 3144-3157, doi:10.1021/ja110545h (2011).
12 Shi, D., Nannenga, B. L., Iadanza, M. G. & Gonen, T. Three-dimensional electron crystallography of protein microcrystals. *eLife* 2, e01345, doi:10.7554/eLife.01345 (2013).
13 Rodriguez, J. A. et al. Structure of the toxic core of [agr]-synuclein from invisible crystals. *Nature* 525, 486-490, doi:10.1038/nature15368 (2015).
14 Rodriguez, J. A. & Gonen, T. in *Methods in Enzymology* Vol. Volume 579 (ed R. A. Crowther) 369-392 (Academic Press, 2016).
15 Eisenberg, D. S. & Sawaya, M. R. in *Annu. Rev. Biochem.* 3.1-3.27 (2017).
16 Wood, S. J., Wetzel, R., Martin, J. D. & Hurle, M. R. Prolines and Aamyloidogenicity in Fragments of the Alzheimer's Peptide .beta./A4. *Biochemistry* 34, 724-730, doi:10.1021/bi00003a003 (1995).
17 Moore, C. L. et al. Secondary nucleating sequences affect kinetics and thermodynamics of tau aggregation. *Biochemistry* 50, 10876-10886, doi:10.1021/bi2014745 (2011).
18 von Bergen, M. et al. Mutations of Tau Protein in Frontotemporal Dementia Promote Aggregation of Paired Helical Filaments by Enhancing Local β-Structure. *Journal of Biological Chemistry* 276, 48165-48174 (2001).
19 Margittai, M. & Langen, R. Fibrils with parallel in-register structure constitute a major class of amyloid fibrils: molecular insights from electron paramagnetic resonance spectroscopy. *Quarterly Reviews of Biophysics* 41, 265-297, doi:10.1017/S0033583508004733 (2008).
20 Mirbaha, H., Holmes, B. B., Sanders, D. W., Bieschke, J. & Diamond, M. I. Tau trimers are the minimal propagation unit spontaneously internalized to seed intracellular aggregation. *Journal of Biological Chemistry*, doi: 10.1074/jbc.M115.652693 (2015).
21 Kfoury, N., Holmes, B. B., Jiang, H., Holtzman, D. M. & Diamond, M. I. Trans-cellular Propagation of Tau Aggregation by Fibrillar Species. *The Journal of Biological Chemistry* 287, 19440-19451, doi:10.1074/jbc.M112.346072 (2012).

22 Sanders, David W. et al. Distinct Tau Prion Strains Propagate in Cells and Mice and Define Different Tauopathies. *Neuron* 82, 1271-1288, doi:http://dx.doi.org/10.1016/j.neuron.2014.04.047 (2014).

23 Siddiqua, A. et al. Conformational Basis for Asymmetric Seeding Barrier in Filaments of Three- and Four-Repeat Tau. *Journal of the American Chemical Society* 134, 10271-10278, doi:10.1021/ja303498q (2012).

24 Margittai, M. & Langen, R. Template-assisted filament growth by parallel stacking of tau. *Proceedings of the National Academy of Sciences of the United States of America* 101, 10278-10283, doi:10.1073/pnas.0401911101 (2004).

25 Kaufman, Sarah K. et al. Tau Prion Strains Dictate Patterns of Cell Pathology, Progression Rate, and Regional Vulnerability In Vivo. *Neuron* 92, 796-812, doi:http://dx.doi.org/10.1016/j.neuron.2016.09.055 (2016).

26 Wiltzius, J. J. W. et al. Molecular mechanisms for protein-encoded inheritance. *Nat Struct Mol Biol* 16, 973-978, doi:http://www.nature.com/nsmb/journal/v16/n9/suppinfo/nsmb.1643_S1.html (2009).

27 Kabsch, W. XDS. *Acta Crystallographica Section D: Biological Crystallography* 66, 125-132, doi:10.1107/50907444909047337 (2010).

28 McCoy, A. J. et al. Phaser crystallographic software. *Journal of Applied Crystallography* 40, 658-674, doi: 10.1107/50021889807021206 (2007).

29 Murshudov, G. N., Vagin, A. A. & Dodson, E. J. Refinement of Macromolecular Structures by the Maximum-Likelihood Method. *Acta Crystallographica Section D* 53, 240-255, doi:doi:10.1107/S0907444996012255 (1997).

30 Bricogne G., B. E., Brandi M., Flensburg C., Keller P., Paciorek W., Roversi P, Sharff A., Smart O. S., Vonrhein C., Womack T. O. BUSTER 2.10.0. Cambridge, United Kingdom: Global Phasing Ltd. (2016).

31 Emsley, P., Lohkamp, B., Scott, W. G. & Cowtan, K. Features and development of *Coot*. *Acta Crystallographica Section D* 66, 486-501, doi:doi:10.1107/50907444910007493 (2010).

32 Biernat, J. et al. The switch of tau protein to an Alzheimer-like state includes the phosphorylation of two serine-proline motifs upstream of the microtubule binding region. *The EMBO Journal* 11, 1593-1597 (1992).

REFERENCES

Note: This application references a number of different publications as indicated throughout the specification by reference numbers. A list of these different publications ordered according to these reference numbers can be found above.

All publications mentioned herein (e.g. Seidler et al., Nat Chem. 2018 February; 10(2):170-176) are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further, the actual publication dates may be different from those shown and require independent verification.

CONCLUSION

This concludes the description of the preferred embodiment of the present invention. The foregoing description of one or more embodiments of the invention has been presented for the purposes of illustration and description. It is not intended to be exhaustive or to limit the invention to the precise form disclosed. Many modifications and variations are possible in light of the above teaching.

The invention claimed is:

1. A composition comprising: a peptide comprising the amino acid sequence: DVQMINKKRK (SEQ ID NO: 2), DVQWINKKRK (SEQ ID NO: 3), or DVWMINKKRK (SEQ ID NO: 5); and a pharmaceutically acceptable carrier including a peptide stabilizing excipient.

2. The composition of claim 1, wherein the peptide comprises the amino acid sequence: DVQMINKKRK (SEQ ID NO: 2).

3. The composition of claim 1, wherein the peptide comprises the amino acid sequence: DVQWINKKRK (SEQ ID NO: 3).

4. The composition of claim 1, wherein the peptide comprises the amino acid sequence: DVWMINKKRK (SEQ ID NO: 5).

5. The composition of claim 1, wherein the composition further comprises a peptide comprising the amino acid sequence:
DVQRINKKRK (SEQ ID NO: 4)
DVWWINKKRK (SEQ ID NO: 6)
DVWMWNKKRK (SEQ ID NO: 7);
DVWWWNKKRK (SEQ ID NO: 8); and
VQIVYK (SEQ ID NO: 9).

6. The composition of claim 1, wherein the peptide stabilizing excipient comprises a preservative, a tonicity adjusting agent, a detergent, a hydrogel, a viscosity adjusting agent, or a pH adjusting agent.

7. The composition of claim 1, wherein the peptide is coupled to a cell penetrating peptide (CPP).

8. The composition of claim 7, wherein the CPP is less than 30 amino acids in length.

9. The composition of claim 7, wherein the CPP comprises a plurality of arginine residues.

10. The composition of claim 1, wherein the peptide comprises a D amino acid.

* * * * *